(12) United States Patent
Backus et al.

(10) Patent No.: US 9,788,942 B2
(45) Date of Patent: Oct. 17, 2017

(54) PROSTHETIC HEART VALVE HAVING TUBULAR SEAL

(71) Applicant: BOSTON SCIENTIFIC SCIMED, INC., Maple Grove, MN (US)

(72) Inventors: Andrew J. H. Backus, Santa Cruz, CA (US); Spencer C. Noe, Santa Cruz, CA (US); Christopher M. Miracle, Walnut Creek, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 1 day.

(21) Appl. No.: 15/007,979

(22) Filed: Jan. 27, 2016

(65) Prior Publication Data

US 2016/0220365 A1    Aug. 4, 2016

Related U.S. Application Data

(60) Provisional application No. 62/111,472, filed on Feb. 3, 2015.

(51) Int. Cl.
*A61F 2/24*     (2006.01)
*A61F 2/90*     (2013.01)

(52) U.S. Cl.
CPC .......... *A61F 2/2418* (2013.01); *A61F 2/2415* (2013.01); *A61F 2/2436* (2013.01);
(Continued)

(58) Field of Classification Search
CPC ................................ A61F 2/24; A61F 2/2418
(Continued)

(56) References Cited

U.S. PATENT DOCUMENTS

| 51,922 A | 6/1856 | Peale |
|---|---|---|
| 2,682,057 A | 6/1954 | Lord |

(Continued)

FOREIGN PATENT DOCUMENTS

| CN | 1338951 A | 3/2002 |
|---|---|---|
| DE | 19532846 A1 | 3/1997 |

(Continued)

OTHER PUBLICATIONS

US 8,062,356, 11/2011, Salahieh et al. (withdrawn)
(Continued)

*Primary Examiner* — Suzette J Gherbi
(74) *Attorney, Agent, or Firm* — Seager, Tufte & Wickhem, LLP

(57) ABSTRACT

A prosthetic heart valve includes a plurality of leaflets and an expandable member including one or more braided wires with a first set of wire segments extended helically in a first direction and a second set of wire segments extended helically in a second direction such that each wire segment of the first set intersects a plurality of wire segments from the second set at a plurality of intersection points. The one or more braided wires can have crowns where the wire segments of the first set connect to wire segments of the second set. The heart valve can include a tubular seal secured to the plurality of leaflets and to the expandable member by a plurality of sutures. The sutures can include cross stitches formed around both a wire segment of the first set and a wire segment of the second set at one of the intersection points.

19 Claims, 18 Drawing Sheets

(52) U.S. Cl.
CPC ......... *A61F 2/90* (2013.01); *A61F 2210/0057* (2013.01); *A61F 2220/0075* (2013.01); *A61F 2250/0069* (2013.01)

(58) Field of Classification Search
USPC .............................................. 623/1.15–1.53
See application file for complete search history.

(56) References Cited

U.S. PATENT DOCUMENTS

| | | |
|---|---|---|
| 2,701,559 A | 2/1955 | Cooper |
| 2,832,078 A | 4/1958 | Williams |
| 3,099,016 A | 7/1963 | Edwards |
| 3,113,586 A | 12/1963 | Edmark, Jr. |
| 3,130,418 A | 4/1964 | Head et al. |
| 3,143,742 A | 8/1964 | Cromie |
| 3,334,629 A | 8/1967 | Cohn |
| 3,367,364 A | 2/1968 | Cruz, Jr. et al. |
| 3,409,013 A | 11/1968 | Berry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Van Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | Dipisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,500,014 A | 3/1996 | Quijano et al. |
| 5,507,767 A | 4/1996 | Maeda et al. |
| 5,534,007 A | 7/1996 | St. Germain et al. |

(56) References Cited

U.S. PATENT DOCUMENTS

| | | |
|---|---|---|
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,772,609 A | 6/1998 | Nguyen et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,059,827 A | 5/2000 | Fenton, Jr. |
| 6,074,418 A | 6/2000 | Buchanan et al. |
| 6,093,203 A | 7/2000 | Uflacker |
| 6,096,074 A | 8/2000 | Pedros |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | De Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |

(56) References Cited

U.S. PATENT DOCUMENTS

| | | |
|---|---|---|
| 6,508,803 B1 | 1/2003 | Horikawa et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,773,454 B2 | 8/2004 | Wholey et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,821,297 B2 | 11/2004 | Snyders |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,097,658 B2 | 8/2006 | Oktay |
| 7,122,020 B2 | 10/2006 | Mogul |
| 7,125,418 B2 | 10/2006 | Duran et al. |
| 7,141,063 B2 | 11/2006 | White et al. |
| 7,166,097 B2 | 1/2007 | Barbut |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,674,282 B2 | 3/2010 | Wu et al. |
| 7,712,606 B2 | 5/2010 | Salahieh et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |

(56) References Cited

U.S. PATENT DOCUMENTS

| | | |
|---|---|---|
| 7,846,204 B2 | 12/2010 | Letac et al. |
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0111146 A1 | 6/2004 | McCullagh et al. |
| 2004/0116951 A1 | 6/2004 | Rosengart |
| 2004/0117004 A1 | 6/2004 | Osborne et al. |
| 2004/0117009 A1 | 6/2004 | Cali et al. |

(56) References Cited

U.S. PATENT DOCUMENTS

| | | |
|---|---|---|
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225352 A1* | 11/2004 | Osborne ............... A61F 2/2418 623/1.24 |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0027348 A1* | 2/2005 | Case .................... A61F 2/2412 623/1.24 |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | Wasdyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |

(56) References Cited

U.S. PATENT DOCUMENTS

| | | | |
|---|---|---|---|
| 2008/0269878 A1 | 10/2008 | Iobbi | |
| 2008/0288054 A1 | 11/2008 | Pulnev et al. | |
| 2009/0005863 A1 | 1/2009 | Goetz et al. | |
| 2009/0030512 A1 | 1/2009 | Thielen et al. | |
| 2009/0054969 A1 | 2/2009 | Salahieh et al. | |
| 2009/0076598 A1 | 3/2009 | Salahieh et al. | |
| 2009/0093877 A1 | 4/2009 | Keidar et al. | |
| 2009/0171456 A1 | 7/2009 | Kveen et al. | |
| 2009/0222076 A1 | 9/2009 | Figulla et al. | |
| 2009/0264759 A1 | 10/2009 | Byrd | |
| 2009/0264997 A1 | 10/2009 | Salahieh et al. | |
| 2009/0299462 A1 | 12/2009 | Fawzi et al. | |
| 2010/0049313 A1 | 2/2010 | Alon et al. | |
| 2010/0094399 A1 | 4/2010 | Dorn et al. | |
| 2010/0121434 A1 | 5/2010 | Paul et al. | |
| 2010/0191326 A1 | 7/2010 | Alkhatib | |
| 2010/0219092 A1 | 9/2010 | Salahieh et al. | |
| 2010/0280495 A1 | 11/2010 | Paul et al. | |
| 2011/0257735 A1 | 10/2011 | Salahieh et al. | |
| 2011/0276122 A1* | 11/2011 | Schlick | A61F 2/07 623/1.13 |
| 2011/0276129 A1 | 11/2011 | Salahieh et al. | |
| 2012/0016469 A1 | 1/2012 | Salahieh et al. | |
| 2012/0016471 A1 | 1/2012 | Salahieh et al. | |
| 2012/0022642 A1 | 1/2012 | Haug et al. | |
| 2012/0029627 A1 | 2/2012 | Salahieh et al. | |
| 2012/0041549 A1 | 2/2012 | Salahieh et al. | |
| 2012/0041550 A1 | 2/2012 | Salahieh et al. | |
| 2012/0046740 A1 | 2/2012 | Paul et al. | |
| 2012/0053683 A1 | 3/2012 | Salahieh et al. | |
| 2012/0089224 A1 | 4/2012 | Haug et al. | |
| 2012/0132547 A1 | 5/2012 | Salahieh et al. | |
| 2012/0197379 A1 | 8/2012 | Laske et al. | |
| 2012/0330409 A1 | 12/2012 | Haug et al. | |
| 2013/0013057 A1 | 1/2013 | Salahieh et al. | |
| 2013/0018457 A1 | 1/2013 | Gregg et al. | |
| 2013/0030520 A1 | 1/2013 | Lee et al. | |
| 2013/0123796 A1 | 5/2013 | Sutton et al. | |
| 2013/0158656 A1 | 6/2013 | Sutton et al. | |
| 2013/0190865 A1 | 7/2013 | Anderson | |
| 2013/0304199 A1 | 11/2013 | Sutton et al. | |
| 2014/0018911 A1 | 1/2014 | Zhou et al. | |
| 2014/0094904 A1 | 4/2014 | Salahieh et al. | |
| 2014/0114405 A1 | 4/2014 | Paul et al. | |
| 2014/0114406 A1 | 4/2014 | Salahieh et al. | |
| 2014/0121766 A1 | 5/2014 | Salahieh et al. | |
| 2014/0135912 A1 | 5/2014 | Salahieh et al. | |
| 2014/0243967 A1 | 8/2014 | Salahieh et al. | |
| 2014/0277417 A1 | 9/2014 | Schraut et al. | |
| 2015/0081000 A1* | 3/2015 | Hossainy | A61F 2/88 623/1.2 |
| 2015/0134043 A1* | 5/2015 | Irwin | A61F 2/88 623/1.13 |
| 2016/0256268 A1* | 9/2016 | Dakin | A61B 17/12122 |
| 2016/0296329 A1* | 10/2016 | Alkhatib | A61F 2/2418 |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1088529 A2 | 4/2001 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1430853 A2 | 6/2004 |
| EP | 1435879 A1 | 7/2004 |
| EP | 1439800 A2 | 7/2004 |
| EP | 1472996 A1 | 11/2004 |
| EP | 1229864 B1 | 4/2005 |
| EP | 1059894 B1 | 7/2005 |
| EP | 1551274 A2 | 7/2005 |
| EP | 1551336 A1 | 7/2005 |
| EP | 1078610 B1 | 8/2005 |
| EP | 1562515 A1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1469797 B1 | 11/2005 |
| EP | 1589924 A1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9829057 A1 | 7/1998 |
| WO | 9836790 A1 | 8/1998 |
| WO | 9850103 A1 | 11/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 9009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03028592 A1 | 4/2003 |
| WO | 03030776 A2 | 4/2003 |
| WO | 03037227 A2 | 5/2003 |

(56) References Cited

FOREIGN PATENT DOCUMENTS

| | | | |
|---|---|---|---|
| WO | 03047648 A2 | 6/2003 |
| WO | 03015851 B1 | 11/2003 |
| WO | 03094793 A1 | 11/2003 |
| WO | 03094797 A1 | 11/2003 |
| WO | 2004006803 A1 | 1/2004 |
| WO | 2004006804 A1 | 1/2004 |
| WO | 2004014256 A1 | 2/2004 |
| WO | 2004019811 A2 | 3/2004 |
| WO | 2004019817 A1 | 3/2004 |
| WO | 2004021922 A2 | 3/2004 |
| WO | 2004023980 A2 | 3/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 7/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005062980 A2 | 7/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2006138391 A2 | 12/2006 |
| WO | 2007033093 A2 | 3/2007 |
| WO | 2007035471 A2 | 3/2007 |
| WO | 2007044285 A2 | 4/2007 |
| WO | 2007053243 A2 | 5/2007 |
| WO | 2007058847 A2 | 5/2007 |
| WO | 2007092354 A2 | 8/2007 |
| WO | 2007097983 A2 | 8/2007 |
| WO | 2010042950 A2 | 4/2010 |
| WO | 2012116368 A2 | 8/2012 |

OTHER PUBLICATIONS

US 8,062,357, 11/2011, Salahieh et al. (withdrawn)
US 8,075,614, 12/2011, Salahieh et al. (withdrawn)
US 8,133,271, 03/2012, Salahieh et al. (withdrawn)
US 8,211,170, 07/2012, Paul et al. (withdrawn)
Andersen et al., "Transluminal implantation of artificial heart valves. Description of a new expandable aortic valve and initial results with implantation by catheter technique in closed chest pigs." Euro. Heart J., 13:704-708, 1992.
Atwood et al., "Insertion of Heart Valves by Catheterization." Project Supervised by Prof. S. Muftu of Northeastern University 2001-2002: 36-40.
Bodnar et al., "Replacement Cardiac Valves R Chapter 13: Extinct Cardiac Valve Prostheses." Pergamon Publishing Corporation. New York, 1991: 307-322.
Boudjemline et al., "Percutaneous Implantation of a Biological Valve in the Aorta to Treat Aortic Valve Insufficiency—A Sheep Study." Med Sci. Monit., vol. 8, No. 4: BR113-116, 2002.
Boudjemline et al., "Percutaneous Implantation of a Valve in the Descending Aorta in Lambs." Euro. Heart J., 23: 1045-1049, 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, 2004.
Boudjemline et al., "Percutaneous Valve Insertion: A New Approach?" J. of Thoracic and Cardio. Surg, 125(3): 741-743, 2003.
Boudjemline et al., "Steps Toward Percutaneous Aortic Valve Replacement." Circulation, 105: 775-778, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, 2004.
Cribier et al., "Percutaneous Transcatheter Implementation of an Aortic Valve Prosthesis for Calcific Aortic Stenosis: First Human Case Description." Circulation, 106: 3006-3008, 2002.
Cribier et al., "Percutaneous Transcatheter Implantation of an Aortic Valve Prosthesis for Calcific Aortic Stenosis: First Human Case." Percutaneous Valve Technologies, Inc., 16 pages, 2002.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Hijazi, "Transcatheter Valve Replacement: A New Era of Percutaneous Cardiac Intervention Begins." J. of Am. College of Cardio., 43(6): 1088-1089, 2004.
Huber et al., "Do Valved Stents Compromise Coronary Flow?" European Journal of Cardio-thoracic Surgery, vol. 25: 754-759, 2004.
Knudsen et al., "Catheter-implanted prosthetic heart valves." Int'l J. of Art. Organs, 16(5): 253-262, 1993.
Kort et al., "Minimally Invasive Aortic Valve Replacement: Echocardiographic and Clinical Results." Am. Heart J., 142(3): 476-481, 2001.
Love et al., The Autogenous Tissue Heart Valve: Current Status. Journal of Cardiac Surgery, 6(4): 499-507, 1991.
Lutter et al., "Percutaneous Aortic Valve Replacement: An Experimental Study. I. Studies on Implantation." J. of Thoracic and Cardio. Surg., 123(4): 768-776, 2002.
Mouloupoulos et al., "Catheter-Mounted Aortic Valves." Annals of Thoracic Surg., 11(5): 423-430, 1971.
Paniagua et al., "Percutaneous Heart Valve in the Chronic in Vitro Testing Model." Circulation, 106: e51-e52, 2002.
Paniagua et al., "Heart Watch." Texas Heart Institute. Spring, 2004. Edition: 8 pages.
Pavcnik et al., "Percutaneous Bioprosthetic Veno Valve: A Long-term Study in Sheep." J. of Vascular Surg., 35(3): 598-603, 2002.
Phillips et al., "A Temporary Catheter-Tip Aortic Valve: Hemodynamic Effects on Experimental Acute Aortic Insufficiency." Annals of Thoracic Surg., 21(2): 134-136, 1976.
Sochman et al., "Percutaneous Transcatheter Aortic Disc Valve Prosthesis Implantation: A Feasibility Study." Cardiovasc. Intervent. Radiol., 23: 384-388, 2000.
Stuart, "In Heart Valves, A Brave, New Non-Surgical World." Start-Up. Sep. 17, 2004.
Vahanian et al., "Percutaneous Approaches to Valvular Disease." Circulation, 109: 1572-1579, 2004.
Van Herwerden et al., "Percutaneous Valve Implantation: Back to the Future?" Euro. Heart J., 23(18): 1415-1416, 2002.
Zhou et al, "Self-expandable Valved Stent of Large Size: Off-Bypass Implantation in Pulmonary Position." Eur. J. Cardiothorac, 24: 212-216, 2003.
Examiner's First Report on AU Patent Application No. 2011202667, issued on May 17, 2012.
"A Matter of Size." Treiennial Review of the National Nanotechnology Initiative, The National Academies Press, Washington DC, v-13, 2006, http://www.nap.edu/catalog/11752la-matter-of-size-triennial-review-of-the-national-nanotechnology.
Atwood et al., "Insertion of Heart Valves by Catheterization." The Capstone Design Course Report. MIME 1501-1502. Technical Design Report. Northeastern University, pp. 1-93, Nov. 5, 2007.
Aug. 19, 2011, Supplemental Search Report from EP Patent Office, EP Application No. 04813777.2.

(56) References Cited

OTHER PUBLICATIONS

Aug. 19, 2011, Supplemental Search Report from EP Patent Office, EP Application No. 04815634.3.
Cunanan et al., "Tissue Characterization and Calcification Potential of Commerical Bioprosthetic Heart Valves." Ann. Thorac. Surg., S417-421, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
EP Search Report mailed Aug. 10, 2011 for EP Application No. 06824992.9.
"Heart Valve Materials—Bovine (cow)." Equine & Porcine Pericardium, Maverick Biosciences Pty. Lt, http://maverickbio.com/biological-medical-device-materials.php?htm. 2009.
Helmus, "Mechanical and Bioprosthetic Heart Valves in Biomaterials for Artificial Organs." Woodhead Publishing Limited: 114-162, 2011.
Hourihan et al., "Transcatheter Umbrella Closure of Valvular and Paravalvular Leaks." JACC, Boston, Massachusetts, 20(6): 1371-1377, Nov. 15, 1992.
Laborde et al., "Percutaneous Implantation of the Corevalve Aortic Valve Prosthesis for Patients Presenting High Risk for Surgical Valve Replacement." EuroIntervention: 472-474, 2006.
Levy, "Mycobacterium Chelonei Infection of Porcine Heart Valves." The New England Journal of Medicine, Washington DC, 297(12), Sep. 22, 1977.
Supplemental Search Report from EP Patent Office, EP Application No. 05758878.2, Oct. 24, 2011.
"Pericardial Heart Valves." Edwards Lifesciences, Cardiovascular Surgery FAQ, Nov. 14, 2010, http://www.edwards.com/products/cardiovascularsurgeryfaq.htm.
Southern Lights Biomaterials Homepage, Jan. 7, 2011, http://www.slv.co.nz/.
Stassano. "Mid-term Results of the Valve-on-Valve Technique for Bioprosthetic Failure." European Journal of cardiothoracic Surgery: 453-457, 2000.
Topol. "Percutaneous Expandable Prosthetic Valves." Textbook of Interventional Cardiology, W.B. Saunders Company, 2: 1268-1276, 1994.
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Bodnar et al., "Replacement Cardiac Valves R Chapter 13: Extinct Cardiac Valve Prostheses." Pergamon Publishing Corporation. New York, 307-322, 1991.
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Hijazi, "Transcatheter Valve Replacement: A New Era of Percutaneous Cardiac Intervention Begins." J. of Am. College of Cardio., 43(6): 1088-1089, Mar. 17, 2004.
Huber et al., "Do Valved Stents Compromise Coronary Flow?" European Journal of Cardio-thoracic Surgery, vol. 25: 754-759, Jan. 23, 2004.
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Moulopoulos et al., "Catheter-Mounted Aortic Valves." Annals of Thoracic Surg., 11(5): 423-430, May 1971.
Paniagua et al., "Percutaneous Heart Valve in the Chronic in Vitro Testing Model." Circulation, 106: e51-e52, Sep. 17, 2002.
Paniagua et al., "Heart Watch." Texas Heart Institute. Edition: 8 pages, Spring, 2004.
Pavcnik et al., "Percutaneous Bioprosthetic Venous Valve: A Long-term Study in Sheep." J. of Vascular Surg., 35(3): 598-603, Mar. 2002.
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Sochman et al., "Percutaneous Transcatheter Aortic Disc Valve Prosthesis Implantation: A Feasibility Study." Cardiovasc. Intervent. Radiol., 23: 384-388, Sep. 2000.
Stuart, "In Heart Valves, A Brave, New Non-Surgical World." Start-Up. Feb. 9-17, 2004.
Stassano. "Mid-term Results of the Valve-on-Valve Technique for Bioprosthetic Failure." European Journal of Cardiothoracic Surgery: vol. 18, 453-457, Oct. 2000.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
Cunanan et al., "Tissue Characterization and Calcification Potential of Commercial Bioprosthetic Heart Valves." Ann. Thorac. Surg., S417-421, May 15, 2001.
"Heart Valve Materials—Bovine (cow)." Equine & Porcine Pericardium, Maverick Biosciences Pty. Lt, http://maverickbio.com/biological-medical-device-materials.php?htm.2009.
Laborde et al., "Percutaneous Implantation of the Corevalve Aortic Valve Prosthesis for Patients Presenting High Risk for Surgical Valve Replacement." EuroIntervention: 472-474, Feb. 2006.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
Zhou et al, "Self-expandable Valved Stent of Large Size: Off-Bypass Implantation in Pulmonary Position." Eur. J. Cardiothorac, 24: 212-216, Aug. 2003.
International Search Report and Written Opinion dated Feb. 13, 2017 for International Application No. PCT/US2016/015288.

* cited by examiner

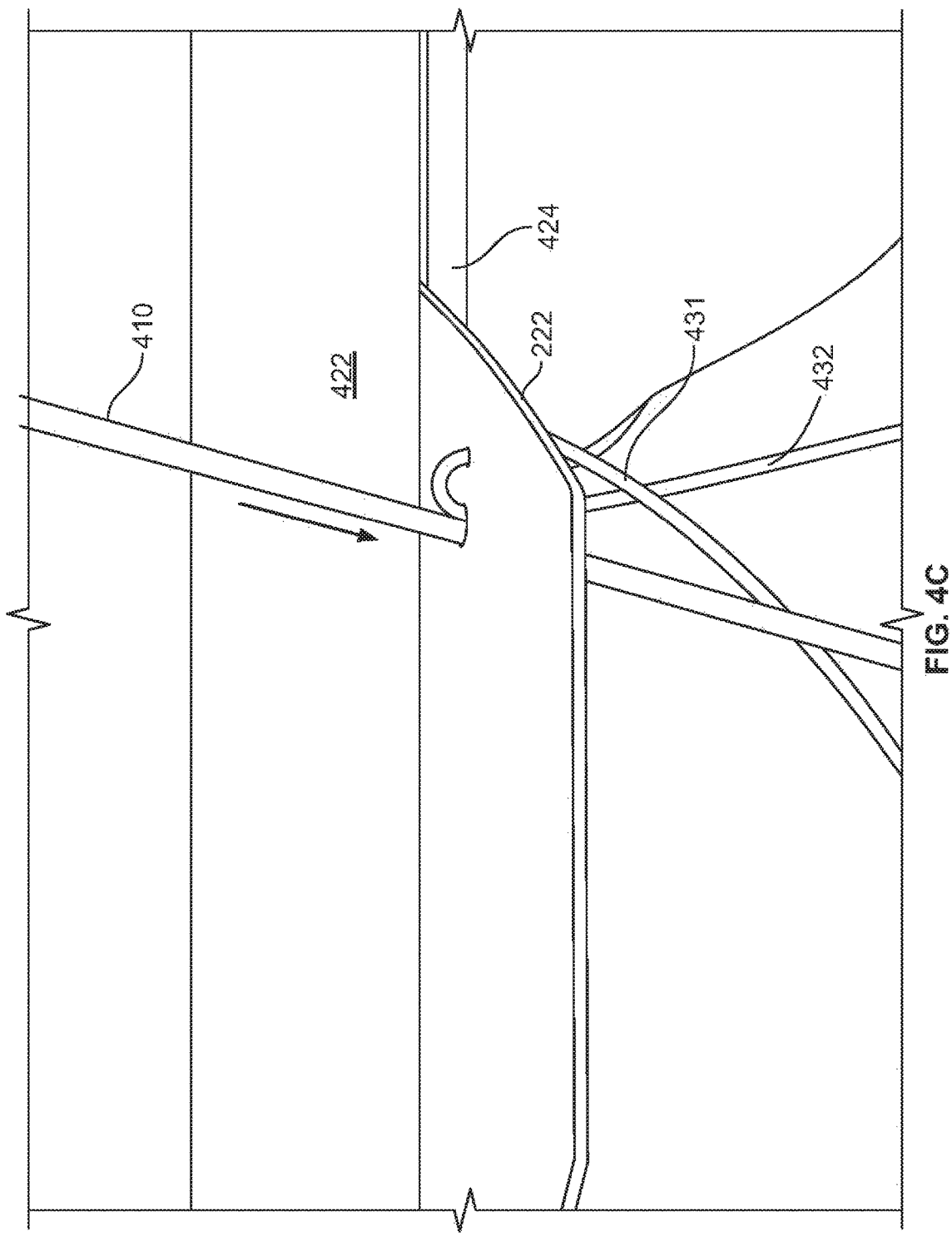

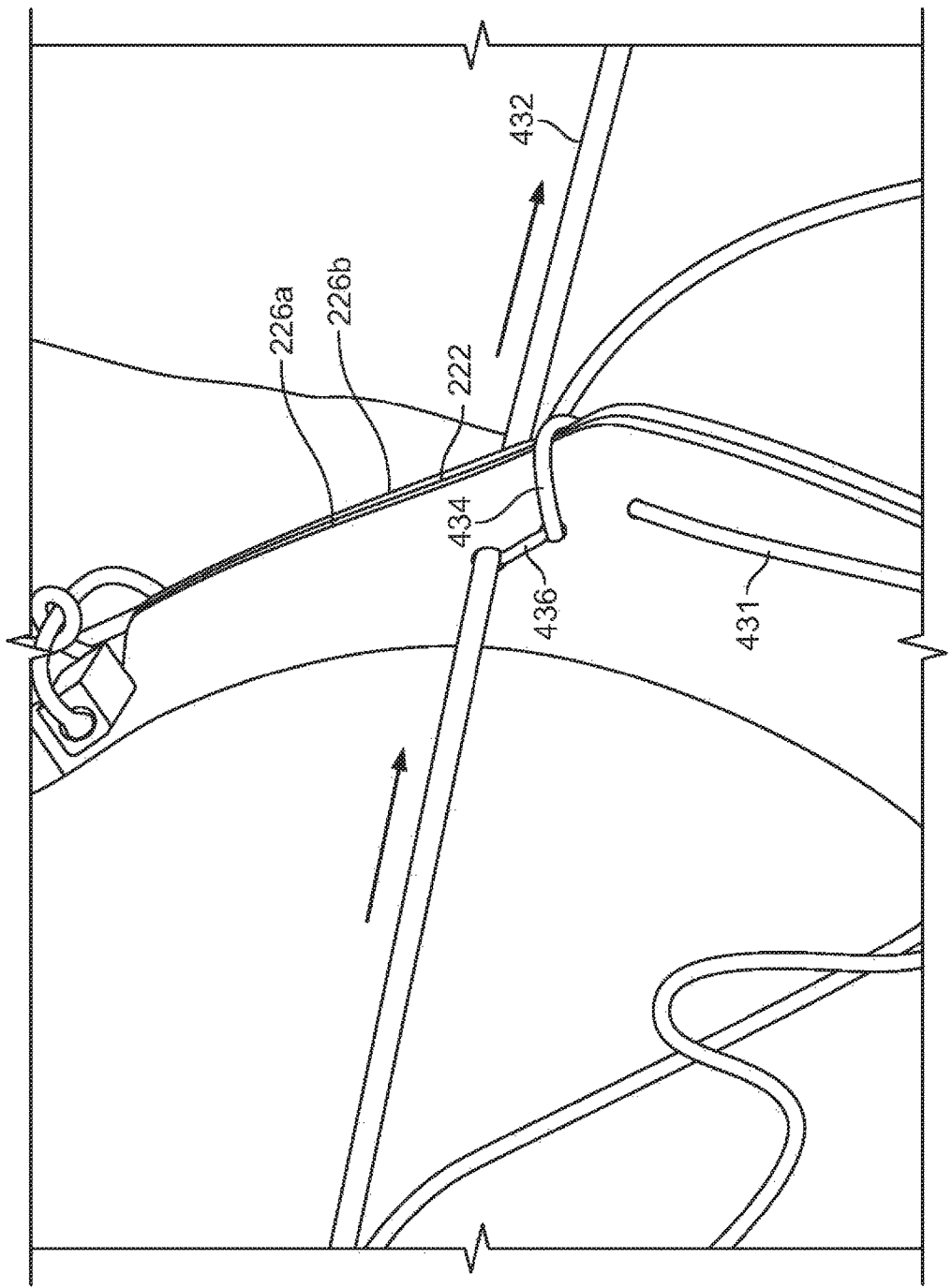

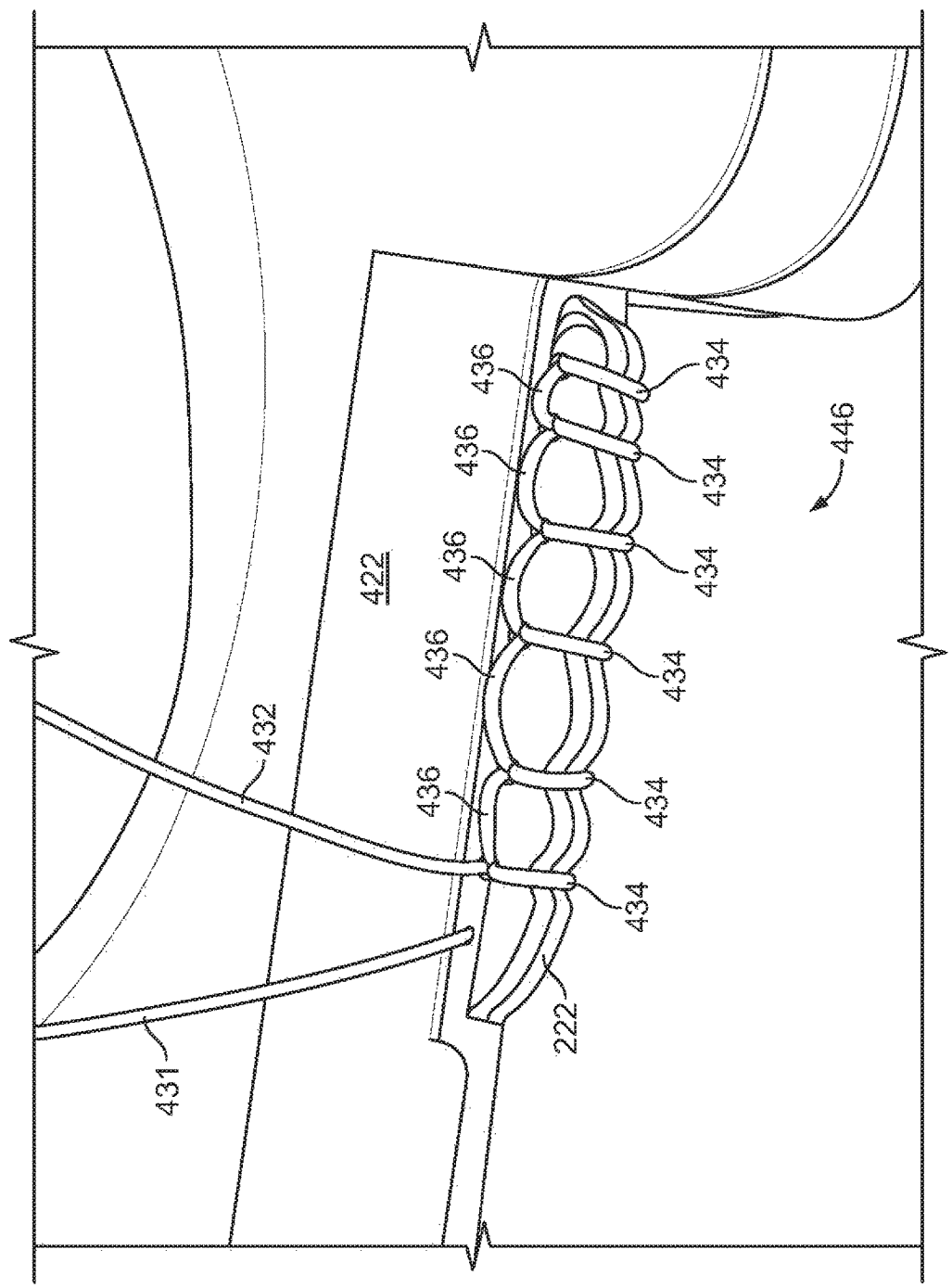

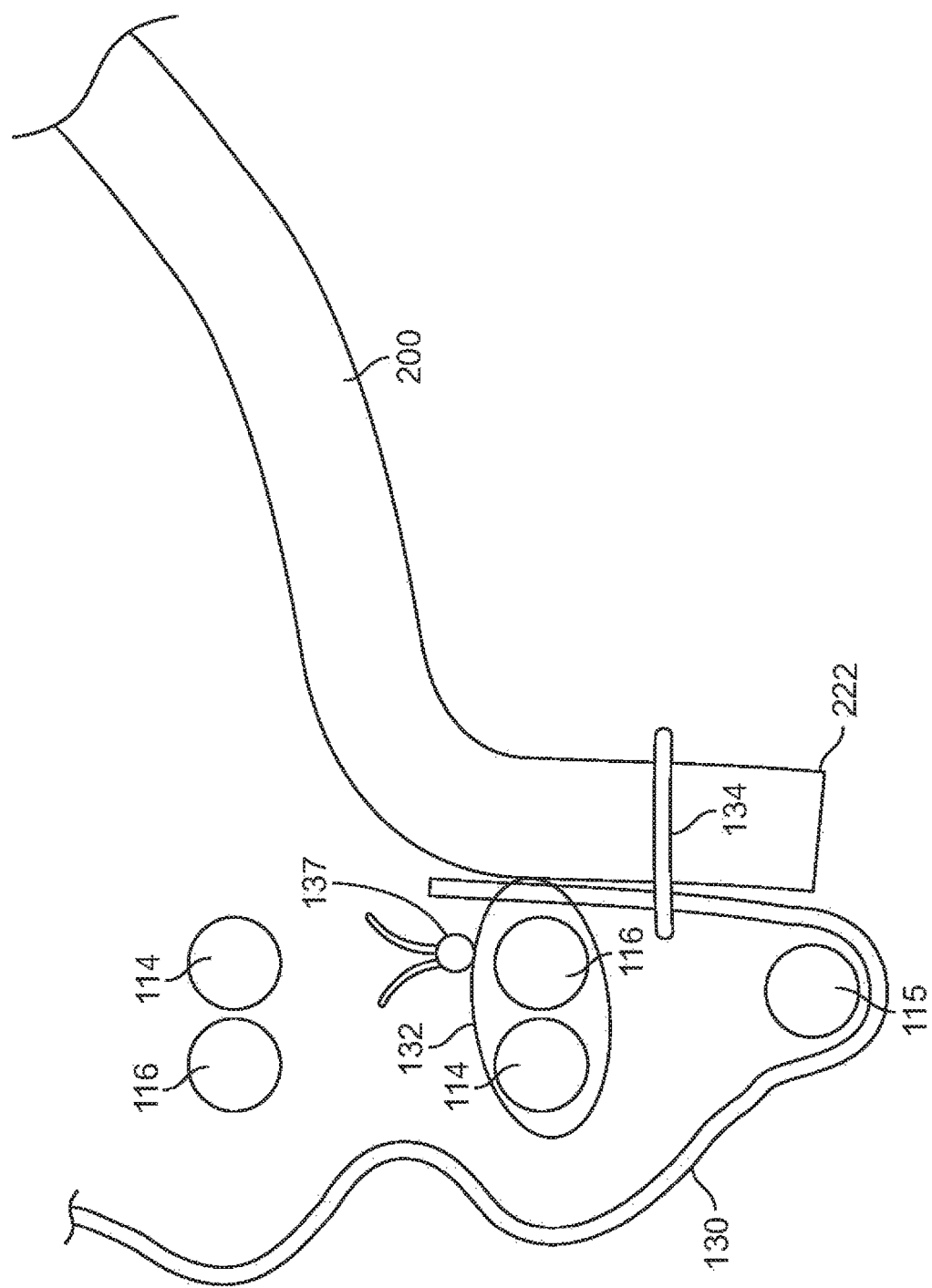

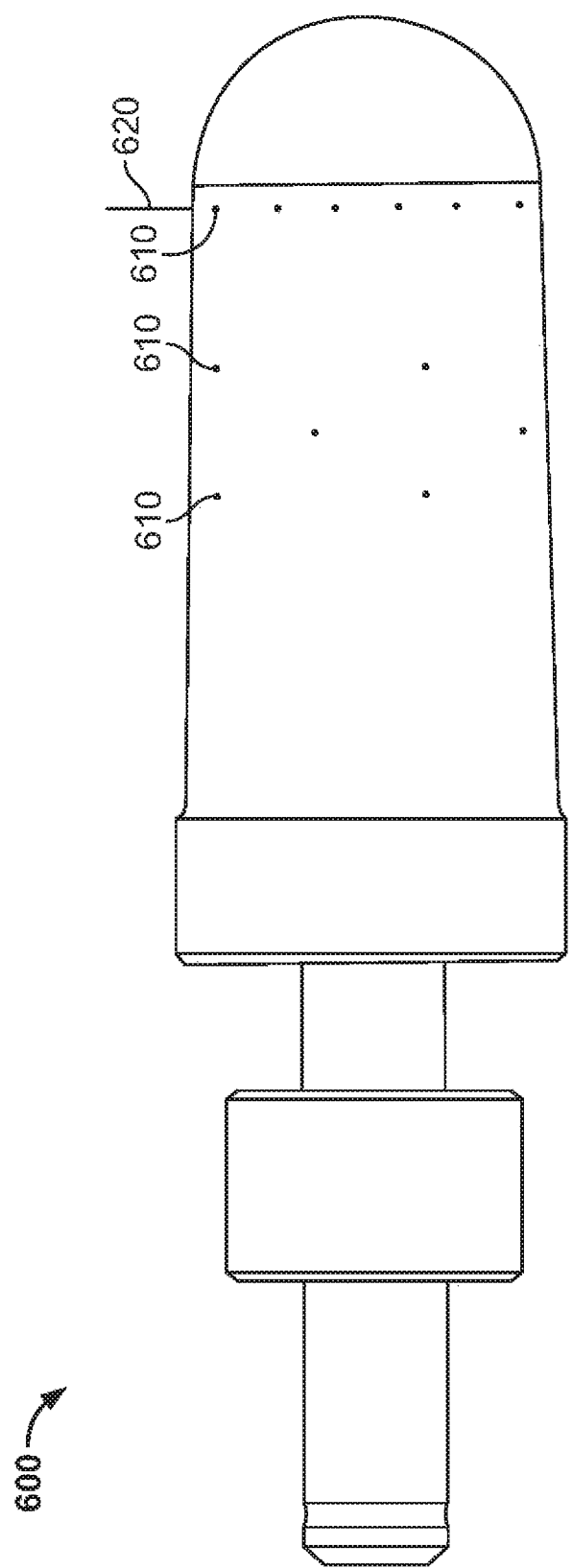

PROSTHETIC HEART VALVE HAVING TUBULAR SEAL

RELATED APPLICATIONS

This application claims the benefit of U.S. Provisional Application No. 62/111,472, file Feb. 3, 2015.

FIELD

This document provides prosthetic heart valves having a tubular seal.

BACKGROUND

The human heart contains four valves: a tricuspid valve, a pulmonic valve, a mitral valve and an aortic valve. The main purpose of the valves is to maintain unimpeded forward flow through the heart and into the major blood vessels connected to the heart, for example, the pulmonary artery and the aorta. As a result of a number of disease processes, both acquired and congenital, any one of the four heart valves may malfunction and result in either stenosis (impeded forward flow) and/or backward flow (regurgitation). Either process burdens the heart and may lead to serious problems, for example, heart failure. Various procedures for fixing or replacing defective heart valves are known in the art. In some cases, artificial heart valves can be implanted in the heart of a patient to replace a diseased or damaged heart valve with a prosthetic equivalent.

Prosthetic heart valves can have a variety of designs. Two major types of prosthetic heart valves include mechanical heart valves and bioprosthetic heart valves. Mechanical heart valves can be made of synthetic materials, such as plastics or metals, while bioprosthetic heart valves can be made of biologic tissue mounted on a fabric covered plastic or metal frame. Bioprosthetic heart valves can include animal tissue, such as porcine or bovine tissue, that has been chemically treated to make the valve suitable for implantation in a human. Bioprosthetic valves do not generally require a patient to undergo anticoagulant therapy, which is typically required when using mechanical valves. As such, there is a need to further improve the design of bioprosthetic valves to retain its functionality during the life of the patient and minimize stenosis and regurgitation.

SUMMARY

Prosthetic heart valves provided herein can have a structure adapted to retain functionality during the life of the patient and minimize stenosis and/or regurgitation by having an improved connection between different parts of a prosthetic heart valve.

In Example 1, a prosthetic heart valve includes an expandable member comprising one or more braided wires, the one or more braided wires comprising a first set of wire segments extended helically in a first direction and a second set of wire segments extended helically in a second direction such that each wire segment of the first set intersects a plurality of wire segments from the second set at a plurality of intersection points, wherein the one or more braided wires have crowns where the wire segments of the first set connect to wire segments of the second set. The prosthetic heart valve can additionally include a plurality of leaflets being secured within the expandable member and a tubular seal comprising an elastomeric material, the tubular seal having an inflow edge being secured to bottom inflow edges of the plurality of leaflets and to the expandable member by a plurality of sutures, characterized by the sutures comprising cross stitches formed around both a wire segment of the first set and a wire segment of the second set at one of the intersection points.

In Example 2, the prosthetic heart valve of Example 1, wherein each cross stitch is an independently tied off stitch unconnected to other cross stitches.

In Example 3, the prosthetic heart valve of either Example 1 or Example 2, wherein each cross stitch is attached at an intersection point immediately adjacent a crown at an inflow side of the expandable member.

In Example 4, the prosthetic heart valve of any of Examples 1-3, wherein the plurality of leaflets are secured together along side edges thereof.

In Example 5, the prosthetic heart valve of Example 4, wherein the plurality of leaflets each comprise two sleeve portions, wherein the sleeve portions are secured to the expandable member by a plurality of anchor elements.

In Example 6, the prosthetic heart valve of any of Examples 1-5, wherein the tubular seal comprises a plurality of non-elastic fibers retained within a matrix of the elastomeric material, the non-elastic fibers being arranged to allow the tubular seal to stretch in an axial or a radial direction.

In Example 7, the prosthetic heart valve of Example 6, wherein the non-elastic fibers are part of a fabric.

In Example 8, the prosthetic heart valve of Example 7, wherein the fabric is a woven fabric.

In Example 9, the prosthetic heart valve of Example 8, wherein the woven fabric comprises fibers in a warp direction and fibers in a waft direction, wherein the fibers in both the warp direction and the waft direction are angled with respect to a central axis of the tubular seal.

In Example 10, the prosthetic heart valve of Example 9, wherein the fibers in both the warp direction and the waft direct are angled at an angle between 5 degrees and 70 degrees with respect to the central axis of the tubular seal.

In Example 11, the prosthetic heart valve of Examples 6-10, wherein the non-elastic fibers are uniformly dispersed throughout the elastomeric polymer matrix.

In Example 12, the prosthetic heart valve of Example 11, wherein the tubular seal has a substantially uniform thickness.

In Example 13, the prosthetic heart valve of any of Examples 1-10, wherein the tubular seal comprises an outflow end region and an inflow end region, the inflow end region being a portion of the tubular seal comprising a fabric within a matrix of the elastomeric matrix, wherein the fabric has a non-linear edge defining an interface between the inflow end region and the outflow end region.

In Example 14, the prosthetic heart valve of Example 13, wherein the non-linear edge of the fabric has a sinusoidal or scalloped shape.

In Example 15, the prosthetic heart valve of any of Example 1-14, wherein the plurality of leaflets are secured to the tubular seal by a continuous circumferential running stitch.

In Example 16, a prosthetic heart valve can include an expandable member comprising one or more braided wires, the one or more braided wires comprising a first set of wire segments extended helically in a first direction and a second set of wire segments extended helically in a second direction such that each wire segment of the first set intersects a plurality of wire segments from the second set at a plurality of intersection points, wherein the one or more braided wires have crowns where the wire segments of the first set connect to wire segments of the second set. The prosthetic heart valve can additionally include a plurality of leaflets being secured within the expandable member and a tubular seal comprising an elastomeric material, the tubular seal having an inflow edge being secured to bottom inflow edges of the plurality of leaflets and to the expandable member by a plurality of sutures, characterized by the sutures comprising cross stitches formed around both a wire segment of the first set and a wire segment of the second set at one of the intersection points.

In Example 17, the prosthetic heart valve of Example 16, wherein each cross stitch is an independently tied off stitch unconnected to other cross stitches.

In Example 18, the prosthetic heart valve of Example 16, wherein each cross stitch is attached at an intersection point immediately adjacent a crown at an inflow side of the expandable member.

In Example 19, the prosthetic heart valve of Example 16, wherein the plurality of leaflets are secured together along side edges thereof.

In Example 20, the prosthetic heart valve of Example 19, wherein the plurality of leaflets each comprise two sleeve portions, wherein the sleeve portions are secured to the expandable member by a plurality of anchor elements.

In Example 21, the prosthetic heart valve of Example 16, wherein the tubular seal comprises a plurality of non-elastic fibers retained within a matrix of the elastomeric material, the non-elastic fibers being arranged to allow the tubular seal to stretch in an axial or a radial direction.

In Example 22, the prosthetic heart valve of Example 21, wherein the non-elastic fibers are part of a fabric.

In Example 23, the prosthetic heart valve of Example 22, wherein the fabric has a thickness ranging from about 40 to about 80 microns.

In Example 24, the prosthetic heart valve of Example 22, wherein the fabric is a woven fabric.

In Example 25, the prosthetic heart valve of Example 24, wherein the woven fabric comprises fibers in a warp direction and fibers in a waft direction, wherein the fibers in both the warp direction and the waft direction are angled with respect to a central axis of the tubular seal.

In Example 26, the prosthetic heart valve of Example 25, wherein the fibers in both the warp direction and the waft direct are angled at an angle between 5 degrees and 70 degrees with respect to the central axis of the tubular seal.

In Example 27, the prosthetic heart valve of Example 22, wherein the fibers are made of polyester.

In Example 28, the prosthetic heart valve of Example 21, wherein the non-elastic fibers are uniformly dispersed throughout the matrix.

In Example 29, the prosthetic heart valve of Example 16, wherein the tubular seal has a substantially uniform thickness.

In Example 30, a prosthetic heart valve includes an expandable member comprising one or more braided wires, the one or more braided wires comprising a first set of wire segments and a second set of wire segments such that each wire segment of the first set intersects a plurality of wire segments from the second set at a plurality of intersection points. The prosthetic heart valve can also include a plurality of leaflets secured within the expandable member and a tubular seal including an elastomeric material. The tubular seal can have an inflow edge being secured to bottom inflow edges of the plurality of leaflets and to the expandable member by a plurality of sutures. The sutures can include cross stitches formed around both a wire segment of the first set and a wire segment of the second set at one of the intersection points, wherein the tubular seal comprises an outflow end region and an inflow end region. The inflow end region can be a portion of the tubular seal including a fabric within a matrix of an elastomeric matrix, wherein the fabric has a non-linear edge defining an interface between the inflow end region and the outflow end region.

In Example 31, the prosthetic heart valve of Example 30, wherein the non-linear edge of the fabric has a sinusoidal or scalloped shape.

In Example 32, the prosthetic heart valve of Example 30, wherein the plurality of leaflets are secured to the tubular seal by a continuous circumferential running stitch.

In Example 33, the prosthetic heart valve of Example 30, wherein the first set of wire segments extends helically in a first direction and a second set of wire segments extends helically in a second direction.

In Example 34, the prosthetic heart valve of Example 33, wherein the one or more braided wires have crowns where the wire segments of the first set connect to wire segments of the second set.

In Example 35, a method of making a tubular seal of a prosthetic heart valve includes forming a tubular seal that includes a fabric within a matrix by dipping a mandrel with a first coating composition that has at least one elastomeric polymer. The method can also include drying the first coating composition. The method can also include positioning the fabric on the mandrel and applying a second coating composition on the mandrel. The second coating composition can be different than the first coating composition. The method can further include removing the tubular seal from the mandrel.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a perspective view of the heart valve connected to the deployment device. FIG. 1B is a side view of the exemplary prosthetic heart valve. FIGS. 1C-1H illustrate how the exemplary heart valve provided herein can be delivered by the deployment device.

FIG. 2A illustrates a rounded notch in a leaflet where a leaflet can be secured to an adjacent leaflet. FIGS. 2B and 2C illustrate a portion of an exemplary leaflet for prosthetic heart valves. FIG. 2B depicts the rounded notch in an armpit of a leaflet. FIG. 2C depicts attachment elements in the armpit of the leaflet.

FIG. 3 depicts apertures in a body of the exemplary leaflet.

FIGS. 4A-4G illustrate how adjacent leaflets can be stitched together in prosthetic heart valves provided herein.

FIGS. 5A-5C illustrate a cross stitch provided herein for connecting a seal to a braided stent in an exemplary prosthetic heart valve provided herein. FIG. 5A shows a front view of a seal having apertures and stitch patterns used for securing the seal to the braided stent. FIG. 5B depicts a close up view of a cross stitch and a portion of a circumferential stitch used for securing the seal to the braided stent. FIG. 5C depicts a cross-sectional view showing the cross stitch and a portion of the circumferential stitch.

FIG. 6 depicts an apparatus that can be used to form a tubular seal provided herein.

Like reference symbols in the various drawings indicate like elements.

DETAILED DESCRIPTION

Prosthetic heart valves provided herein can include a braided stent expandable member secured to a tubular seal using a plurality of cross stitches at a plurality of intersection points of wires of the braided stent. Stitching at intersection points (e.g., intersection points immediately adjacent to inflow crowns) as opposed to at inflow crowns can increase the strength of the attachment while also allowing for improved load transfer to the braided stent. Each stitch, which is described in further detail below, can be formed by passing two stitches of suture in orthogonal directions over the wire intersections, passing through the fabric strip in four locations. Each cross stitch can be individual knotted. In some cases, the cross stitches do not pass through any of the leaflets. The cross stitch can be repeated at many intersections circumferentially around an inflow end of a prosthetic heart valve provided herein until the entire length of the tubular seal is securely attached.

Figure 1A:
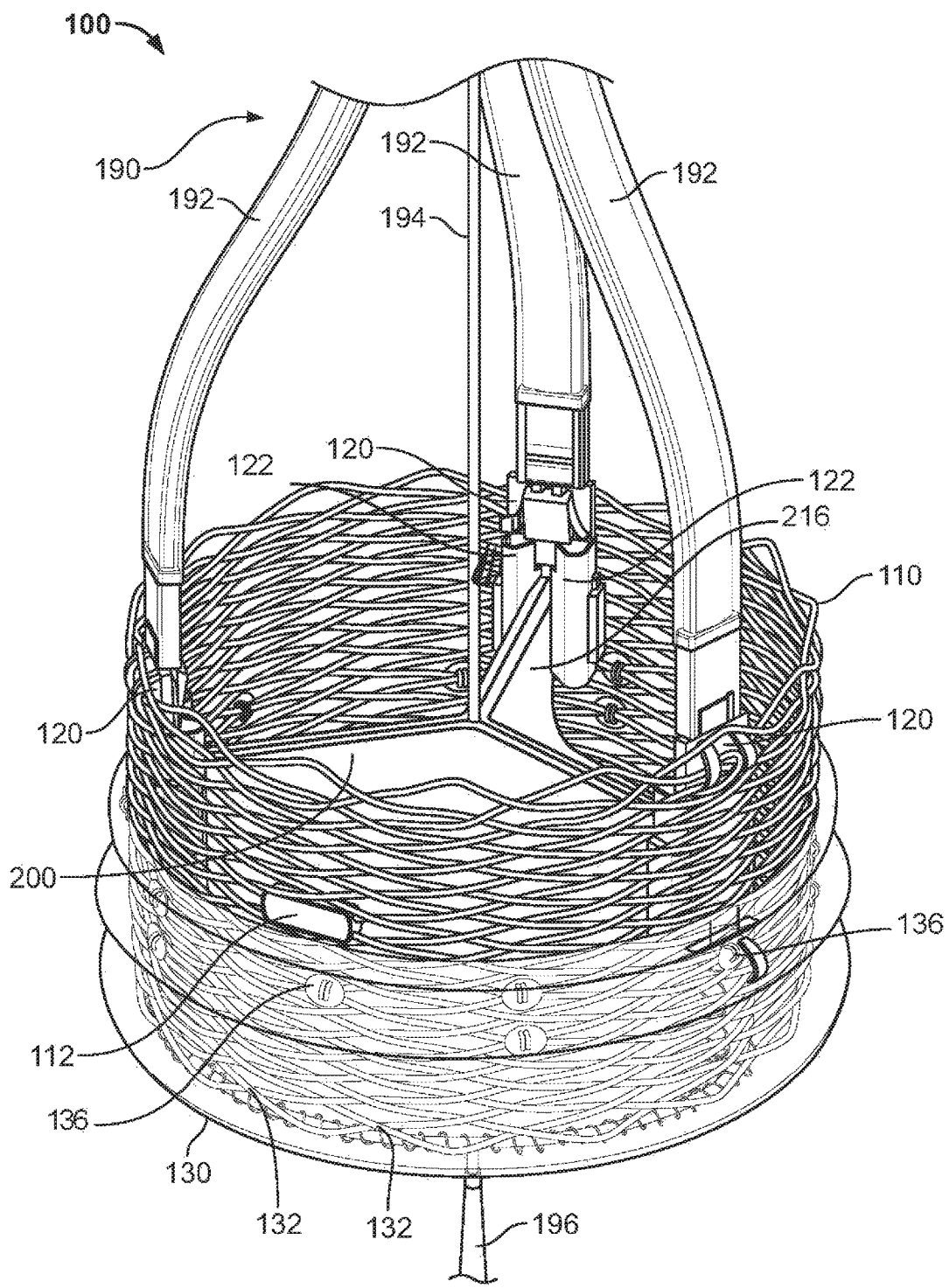
FIGS. 1A-1H illustrate an exemplary prosthetic heart valve and an exemplary deployment device provided herein.
Figure 1B:
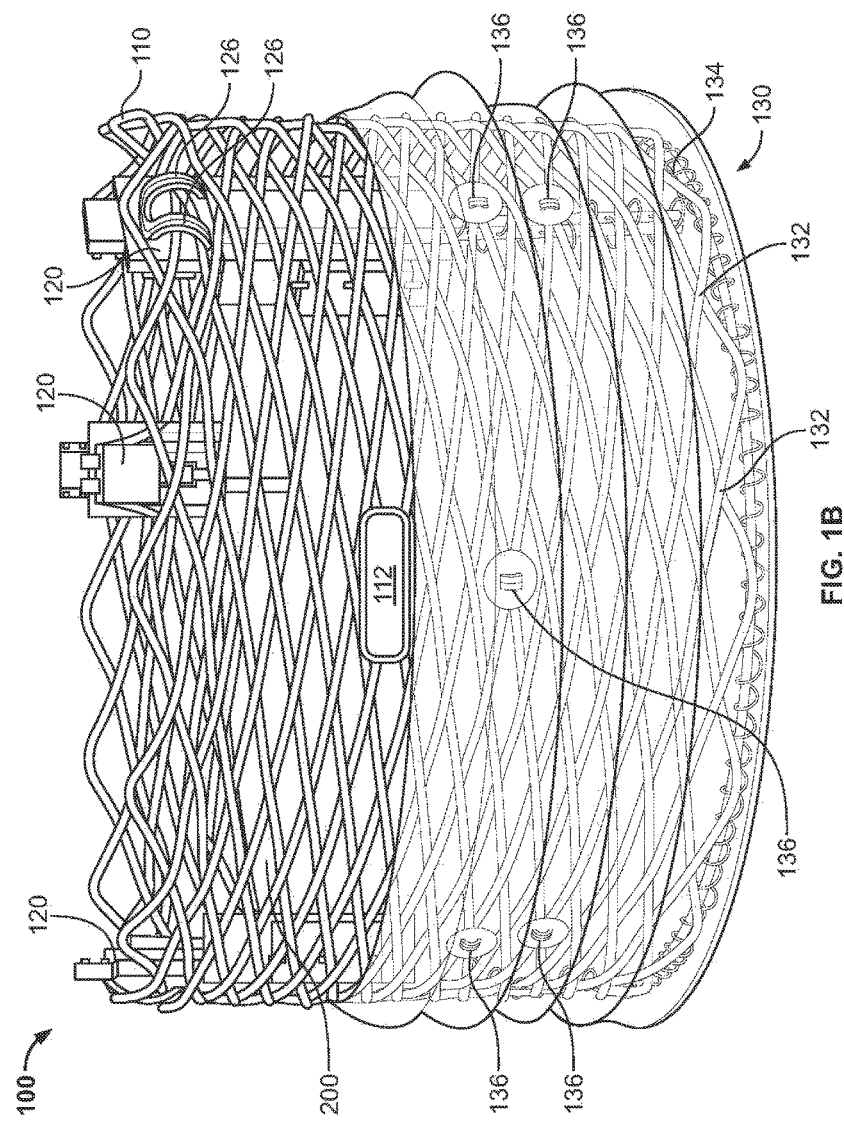
Figure 1C:
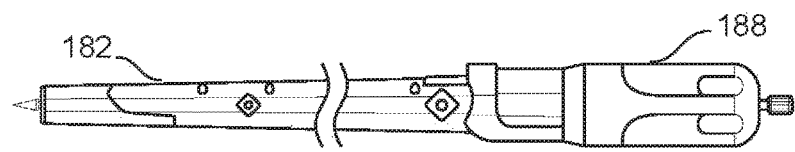
Figure 1D:
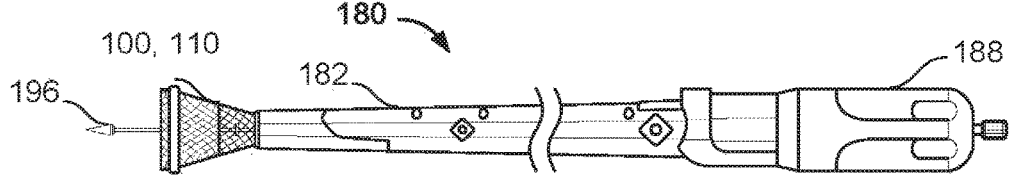
Figure 1E:
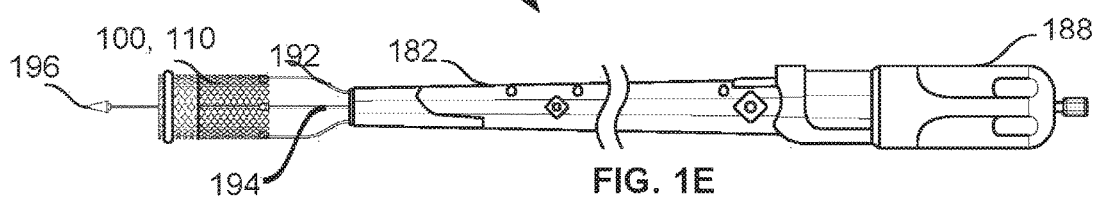
Figure 1F:
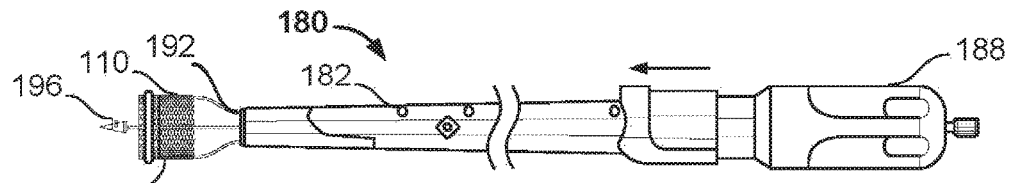
Figure 1G:
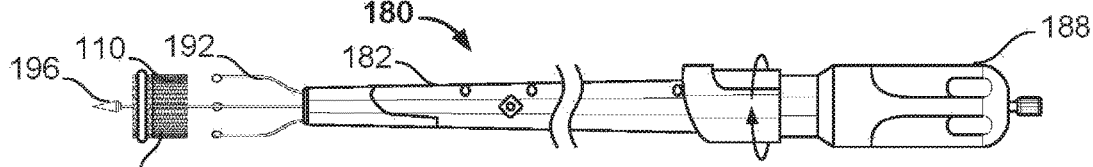
Figure 1H:
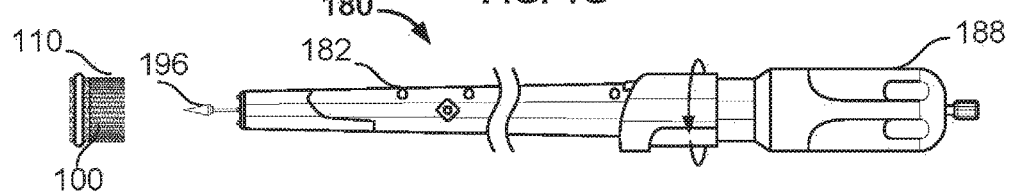

FIGS. 1A and 1B illustrate an exemplary prosthetic heart valve 100 provided herein. FIGS. 1C-1H depict how prosthetic heart valve 100 is deployed. FIG. 1A is a perspective view of prosthetic heart valve 100 connected to a deployment device 190. FIG. 1B is a side view of prosthetic heart valve 100. As shown, prosthetic heart valve 100 includes an expandable member 110, three leaflets 200, three anchor elements 120 that secure sleeve portions 216 of leaflets 200 to expandable member 110, and a tubular seal 130 secured around a blood inflow end of prosthetic heart valve 100. Anchor elements 120 can include post leg compression elements 122 and clamping support structures 126 adapted to provide support along opposite sides of the sleeve portions 216. Expandable member 110 in FIGS. 1A-1D is a braided stent, which is adapted to transition between a restricted state having a smaller diameter and an expanded state having a larger diameter. Expandable member 110 can be self-expanding, mechanically expanded, or a combination thereof.

FIGS. 1C-1H depict how an exemplary heart valve delivery system can deliver the prosthetic heart valve provided herein. As shown in FIGS. 1C-1H, prosthetic heart valve 100 can be deployed using a heart valve delivery system 180. System 180 can include a sheath 182 for retaining the prosthetic heart valve 100 with the expandable member 110 in a restricted state. Within sheath 182, anchor elements 120 (FIGS. 1A and 1B) can be connected to pushing prongs 192 and a pull line 194 can be connected to a nose cap 196, or end cap, which is positioned at the end of the sheath 182. As shown in FIG. 1A, the pull line 194 can extend through expandable member 110 and through the valve opening between the leaflets 200. As shown by FIGS. 1D-1H, once a distal end of sheath 182 is delivered through the circulatory system to an appropriate location (e.g., within the heart), prosthetic heart valve 100 can be deployed. By advancing pushing prongs 192 and pull line 194 relative to sheath 182, prosthetic heart valve 100 can be pushed out of the sheath 182. In some cases, expandable member 110 can self-expand upon exiting sheath 182. In some cases, expandable member 110 can self-expand to a first intermediate diameter, and system 180 can mechanically expand expandable member 110 to a larger deployment diameter. For example, anchor elements 120 can include a locking mechanism to clip a portion of expandable member when the expandable member 110 is expanded to a predetermined locking diameter. In some cases, system 180 can mechanically expand expandable member 110 to a predetermined locking diameter. In some cases, system 180 can compress expandable member 110 between pushing prongs 192 and nose cap 196 by moving pull line 194 relative to pushing prongs 192. The predetermined locking diameter can be adapted to set the diameter of the prosthetic heart valve 100 during implantation. After prosthetic heart valve 100 is set, system 180 can move pull line 194 and nose cap 196 relative to pushing prongs 192 to move the end cap through the opening between leaflets 200 in prosthetic heart valve 100. Pushing prongs 192 can then be retracted from anchor elements 120 and retracted into sheath 182. In some cases, pushing prongs 192 can include a shape member material adapted to help radially expand expandable member 110 as the expandable member 110 exits sheath 182. A control handle 188 can be used to control the relative movements of sheath 182, pushing prongs 192, and pull wire 194. Prosthetic heart valves provided herein can be adapted to mitigate damage that might otherwise occur to valves during delivery and implantation.

In some cases, one or more radiopaque markers can be secured to prosthetic heart valves provided herein. As shown in FIGS. 1A and 1B, expandable member 110 includes a radiopaque marker 112. Any suitable radiopaque material (such as platinum, palladium, gold, tantalum, or alloys thereof) can be used as the radiopaque material in radiopaque marker 112. One or more radiopaque markers can be used with an imaging system to help a physician ensure that a valve is set in an appropriate location. In some cases, prosthetic heart valves provided herein include at least three radiopaque markers.

As shown in FIG. 1A, prosthetic heart valve 100 can include a plurality of leaflets 200. In some cases, as shown, prosthetic heart valve 100 includes three leaflets 200. In some cases, prosthetic heart valves provided herein can have any suitable number of leaflets, such as two, three, four, five, or more leaflets. In some cases, leaflets 200 are secured to one another. In some cases, leaflets 200 can be secured to one another via a plurality of sutures. Leaflets 200 can be sutured along side edges of a body portion of each leaflet. In some cases, prosthetic heart valves provide herein can include a single line of sutures, which can be adapted to minimize leaks, minimize the width of a seam, and/or minimize the profile of a replacement heart valve during percutaneous insertion. In some cases, prosthetic heart valves provide herein can include multiple lines of sutures.

Expandable member 110 can have any suitable structure, arrangement, or material. In some cases, expandable member 110 can include a braided wire stent. For example, U.S. Publication Number 2005/0143809, titled, "Methods and Apparatus for Endovascularly Replacing a Heart Valve," and filed on Nov. 5, 2004, which is herein incorporated by reference for its disclosure of possible structures and materials for a braided wire stent, discloses a braided wire stent. In some cases, expandable member 110 includes a shape memory material (e.g., a nickel-titanium alloy or a cobalt-chromium alloy).

Figure 2B:
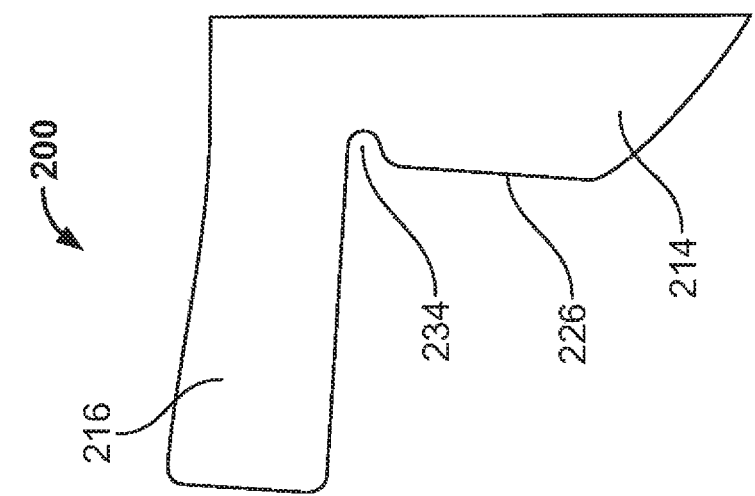
FIGS. 2A-2C illustrates an exemplary leaflet, which can be used in prosthetic heart valves provided herein.
Figure 2A:
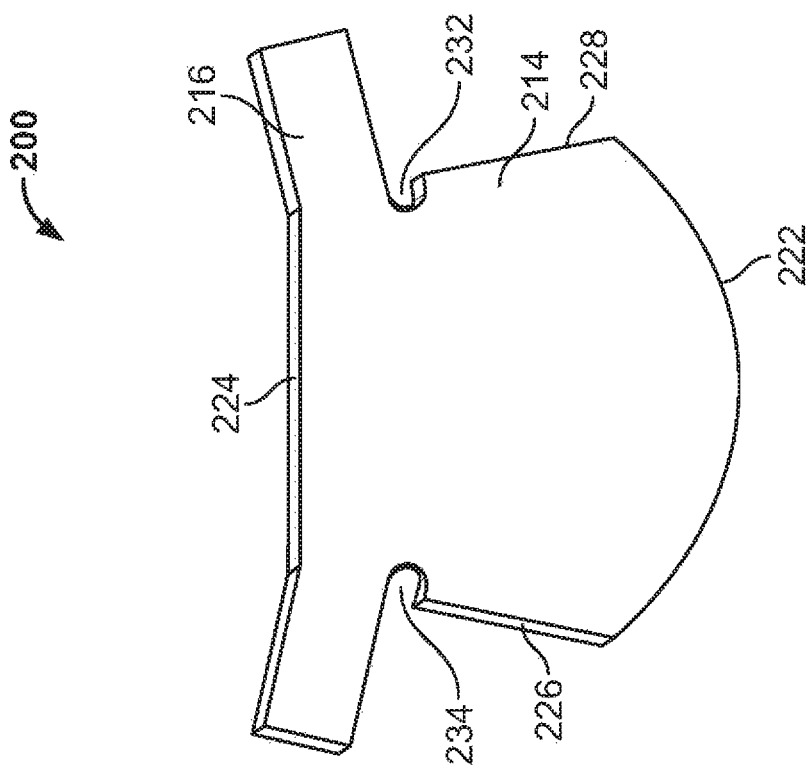
Figure 2C:
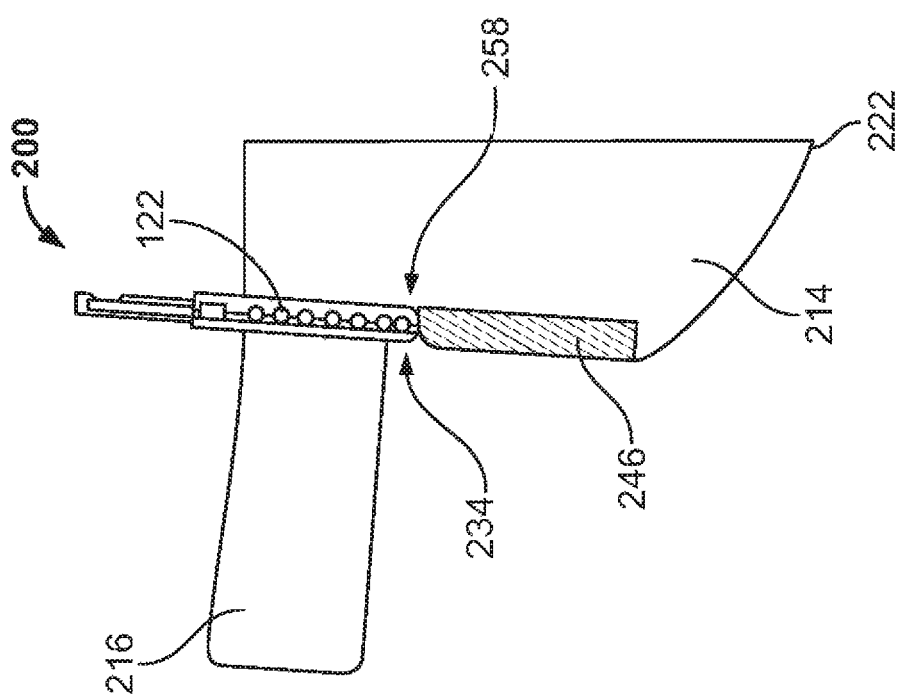

Referring to FIGS. 2A-2C, a leaflet 200 can include a body portion 214 and sleeve portions 216. In some cases, the body portion 214 has a bottom edge 222, a first side edge 226, a second side edge 228, and a free edge 224. Leaflet 200 further includes a front (i.e., the side that blood flows toward), a back (i.e., the side that blood flows away from), a first side adjacent to the first side edge 226, and a second side adjacent to the second side edge 228. In some cases, the front of the leaflet 200 has a different texture than the back. In some cases, for example, the back of the leaflet may be prone to calcium build due to its cusp-shaped surface, therefore it can be beneficial to have a textured surface on the back of the leaflet to mitigate valve calcification issues. In some cases, however, having the back with a non-textured surface can mitigate calcification issues. In some cases, the leaflet 200 is made from tissue obtained from an animal, e.g., a pig or a cow. In some cases, leaflet 200 is made from bovine pericardium. Leaflets 200 can also be made from a synthetic material. Leaflets 200 can be assembled into a heart valve by aligning the opposite side regions of at least two adjacent leaflets 200 and stitching the leaflets 200 together along stitch line 246, as shown in FIG. 2C.

As shown in FIGS. 2A-2C, a prosthetic heart valve can include at least one leaflet 200 having a body portion 214 and two opposite sleeve portions 216. The body portion 214 can be defined by two side edges 226, 228 adjacent each sleeve portion 216. The at least one leaflet 200 can define at least one notch 232, 234 between at least one of the two side edges 226, 228 and the adjacent sleeve portion 216. In other words, each notch 232, 234 can be located along the side edges 228, 226 at a location that is adjacent to the sleeve portions 216, at an armpit of the leaflet 200, as depicted in FIGS. 2A and 2B. In some cases, leaflet 200 can define a notch 232, 234 generally along the side edges 228, 226. In some cases, a notch 232, 234 can be defined along the sleeve portion 216. In some cases, multiple notches 232, 234 can be located along the sleeve portion 216 or one of the side edges 228, 226, and/or at the armpit of the leaflet 200.

As shown in FIGS. 2A and 2B, the body portion 214 of the leaflet can have a conical frustum shape defined by a bottom edge 222, the first side edge 226, the second side edge 228, and a free edge 224. In some cases, other suitable shapes for the body portion can be contemplated, for example, a generally square, rectangular, triangular or trapezoidal shaped body portion.

The sleeve portions, as shown in FIGS. 2A-2C, can extend outwardly from the body portion of the leaflet 200. Each sleeve portion may be angled away from free edge of the body portion. Sleeve portions can be generally rectangular-shaped extensions with lateral ends. In some cases, the sleeve portions can have rounded ends.

Still referring to FIGS. 2A-2C, notches 232, 234 can be generally U-shaped. Other suitable notch shapes can include, but are not limited to, a V-shaped, Z-shaped, rectangular-shaped and an oval-shaped notch. Notches can also have rounded edges to smooth the transition between a notch and the side edges 228, 226 of the leaflet 200. Notches 232, 234 can have a length dimension that can range from about 0.02 inches to about 0.20 inches (or from about 0.5 millimeters (mm) to about 4 mm).

Referring to FIG. 2C, notches 232, 234 can be shaped and sized to accommodate attachment of post leg compression elements 122. Post leg compression elements 122 can be a part of anchor elements 120 (shown in FIGS. 1A and 1B) that compress and restrain sleeve portions 216 along the same line as the stitch line 246. A suture 258 can be used to apply an appropriate and consistent compressive force between the post leg compression elements 122 in order to prevent leakage through sleeve portions 216 of the leaflets 200. Sutures that pierce the body portion 214 at or near the armpit of the leaflet, however, can pull, stretch and abrade the surrounding adjacent tissue, creating stress concentrations at or near the armpit of the leaflet. Stress concentrators can result in tears forming in the leaflet material. Using notches 232 and 234 and post leg compression elements 122, however, can minimize potential heart valve tearing caused by sutures at or near the armpit location. Notches 232, 234 can be positioned proximate to the post leg compression elements near the armpit of the leaflet, e.g., between at least one of the two side edges 226, 228 and the adjacent sleeve portion 216, to create enlarged openings that suture 258 can pass therethrough without pulling or stretching the adjacent tissue. Accordingly, a notched leaflet 200 can improve valve opening capabilities and the reliability of prosthetic heart valves provided herein.

Figure 3:
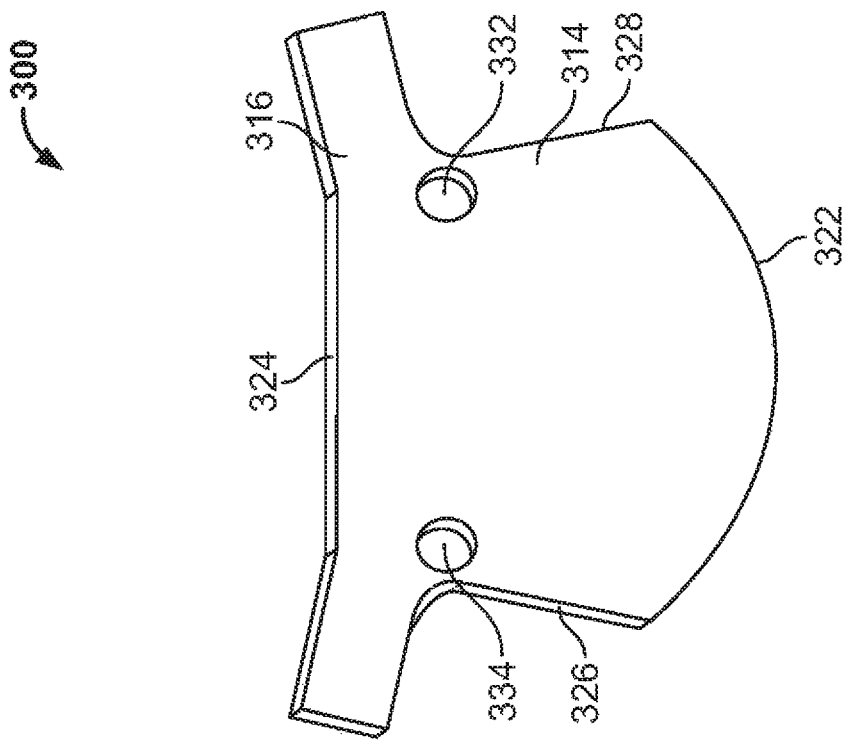
FIG. 3 illustrates another exemplary leaflet, which can be used in prosthetic heart valves provided herein.

FIG. 3 illustrates another exemplary leaflet, which can be used in prosthetic heart valves provided herein. As shown in FIG. 3, leaflet 300 can include a body portion 314 and at least two opposite sleeve portions 316. The body portion 314 can be defined by at least two side edges 326, 328 adjacent each sleeve portion 316. Leaflet 300 can define two apertures 332 and 334. Each aperture 332, 334 can be positioned adjacent the side edges 326, 328 and an adjacent sleeve portion 316. Each aperture 332, 334 can be adapted to secure one leaflet to an adjacent leaflet.

In some cases, the body portion 314 has a bottom edge 322, a first side edge 326, a second side edge 328, and a free edge 324. Leaflet 300 further includes a front, a back, a first side adjacent to the first side edge 326, and a second side adjacent to the second side edge 328. In some cases, the front of the leaflet 300 has a different texture than the back. In some cases, this occurs where the leaflet 300 is made from pig, cow, or other natural animal tissue. In some cases, leaflet 300 is made from bovine pericardium. Leaflets 300 can also be made from a synthetic material. Leaflets 300 can be assembled into a heart valve by aligning the opposite side regions of at least two adjacent leaflets 300 and stitching the leaflets 300 together along stitch line 246, as shown in FIG. 2C.

As shown in FIG. 3, leaflet 300 defines apertures 332 and 334 adjacent the side edges 328, 326 and adjacent the sleeve portions 316. Apertures 332 and 334 can be generally circular in shape. Other suitable aperture shapes can include, for example, a rectangular, an oval, a triangular, or a diamond shape. In some cases, apertures 332, 334 can have a length dimension or a diameter from about 0.02 inches to about 0.20 inches (or from about 0.5 mm to about 4 mm). In some cases, one or more apertures 332, 334 can be located in the side edges 328, 326 and/or the sleeve portions 316 of the leaflet 300. In some cases, multiple apertures can be located in a region that is adjacent to the side edges 328, 326 and the sleeve portions 316.

Apertures 332, 334 in the leaflets 300 can allow one leaflet to be secured to an adjacent leaflet. Similar to the notches discussed above, apertures 332 and 334 can be shaped and sized to accommodate attachment of post leg compression elements 122. Referring back to FIGS. 1A and 1B, post leg compression elements 122 can be a part of anchor elements 120 that compress and restrain sleeve portions 216 along the same line as the stitch line 246. A suture 258 can be used to apply an appropriate and consistent compressive force between the post leg compression elements 122 in order to prevent leakage through sleeve portions 216 of the leaflets 200. As already discussed herein, sutures that pierce the body portion 214 at or near the armpit of the leaflet can create stress concentrations at or near the armpit of the leaflet that may result in tearing. Apertures 332 and 334 and post leg compression elements 122, however, can minimize this potential tearing caused by sutures near the armpit location. Apertures 332, 334 can be positioned proximate to the post leg compression elements near the armpit location to create enlarged openings that suture 258 can pass therethrough without pulling or stretching the adjacent tissue. Accordingly, leaflets 300 used in prosthetic heart valves provided herein can improve the reliability of prosthetic heart valves provided herein.

FIGS. 4A-4G depict how leaflets 200 can be connected (or jointed) with an improved stitch discussed herein. As shown, stitch 446 can be a single continuous line stitch traveling along a stitch line in a forward direction and back in a reverse direction. In some cases, stitch 446 can run along a leaflet from a bottom edge to a side edge of the leaflet (e.g., bottom edge 222 to side edge 226 of leaflet 200 in FIG. 2A-2B). In some cases, stitch 446 can run from a side edge to a notch of a leaflet (e.g., side edge 226 to notch 234 of leaflet 200 in FIG. 2A-2B).

As shown in FIGS. 4D-4G, stitch 446 can include a plurality of perpendicular loop segments 434 extending through an aperture in the two leaflets, around outer side edges of the two attached leaflets, and back through the aperture. Stitch 446 can include a plurality of parallel segments 436 extending between adjacent apertures along the stitch line. Stitch 446 can include two perpendicular loop segments 434 extending through apertures formed in the stitch line. In some cases, a first perpendicular loop segment 434 for a first aperture in the stitch line is formed when the stitch is formed in the forward direction and a second perpendicular loop segment 434 for the first aperture is formed in the reverse direction. In some cases, parallel segments 436 made in a forward direction alternate between opposite sides of the two leaflets between each aperture in the stitch line. In some cases, parallel segments 436 made in a reverse direction are formed on an opposite side of the two leaflets from parallel segments 436 made in a forward direction. In some cases, opposite parallel segments 436 made in the forward and reverse directions can provide a continuous compressive force along the entire length of the stitch line. Perpendicular loop segments 434 can provide compressive force to reinforce a seal formed between the two leaflets along the stitch line.

Stitch 446 can include any appropriate number of perpendicular loop segments formed through any appropriate number of apertures. As shown, stitch 446 includes six perpendicular loop segments formed through six apertures (two perpendicular loop segments per aperture). In some cases, stitch 446 can include up to twelve perpendicular loop segments formed through six or more apertures. In some cases, a stitch connecting side edge segments of leaflets can be formed using between 3 and 20 apertures and include between 3 and 40 perpendicular loop segments. In some cases, apertures can be positioned from about 0.008 inches to about 0.4 inches apart (about 0.2 mm to about 10 mm apart). In some cases, apertures can be positioned from about 0.008 inches to about 0.4 inches (about 0.2 mm to about 10 mm) away from the side edges of the leaflets.

Figure 4A:
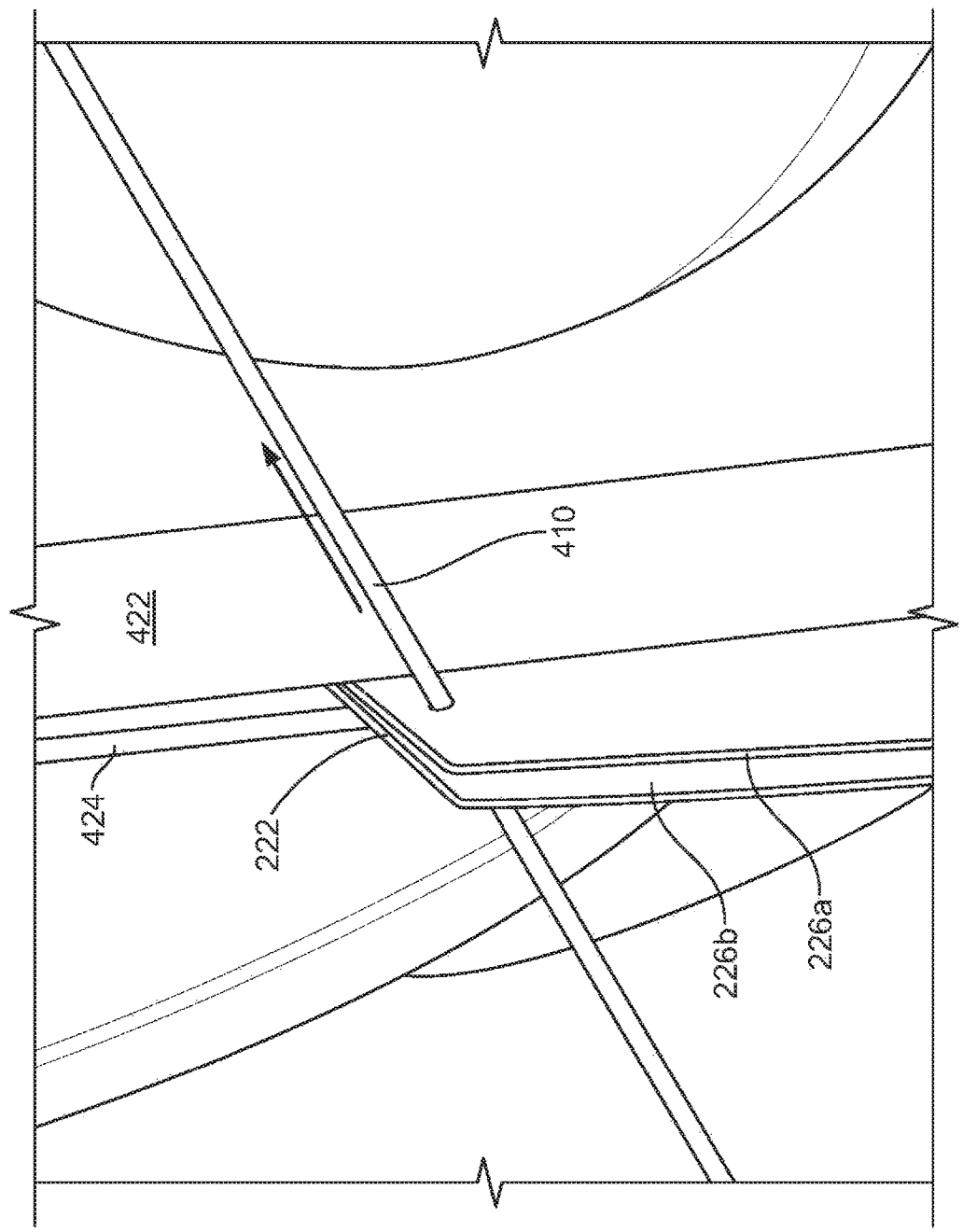
Figure 4B:
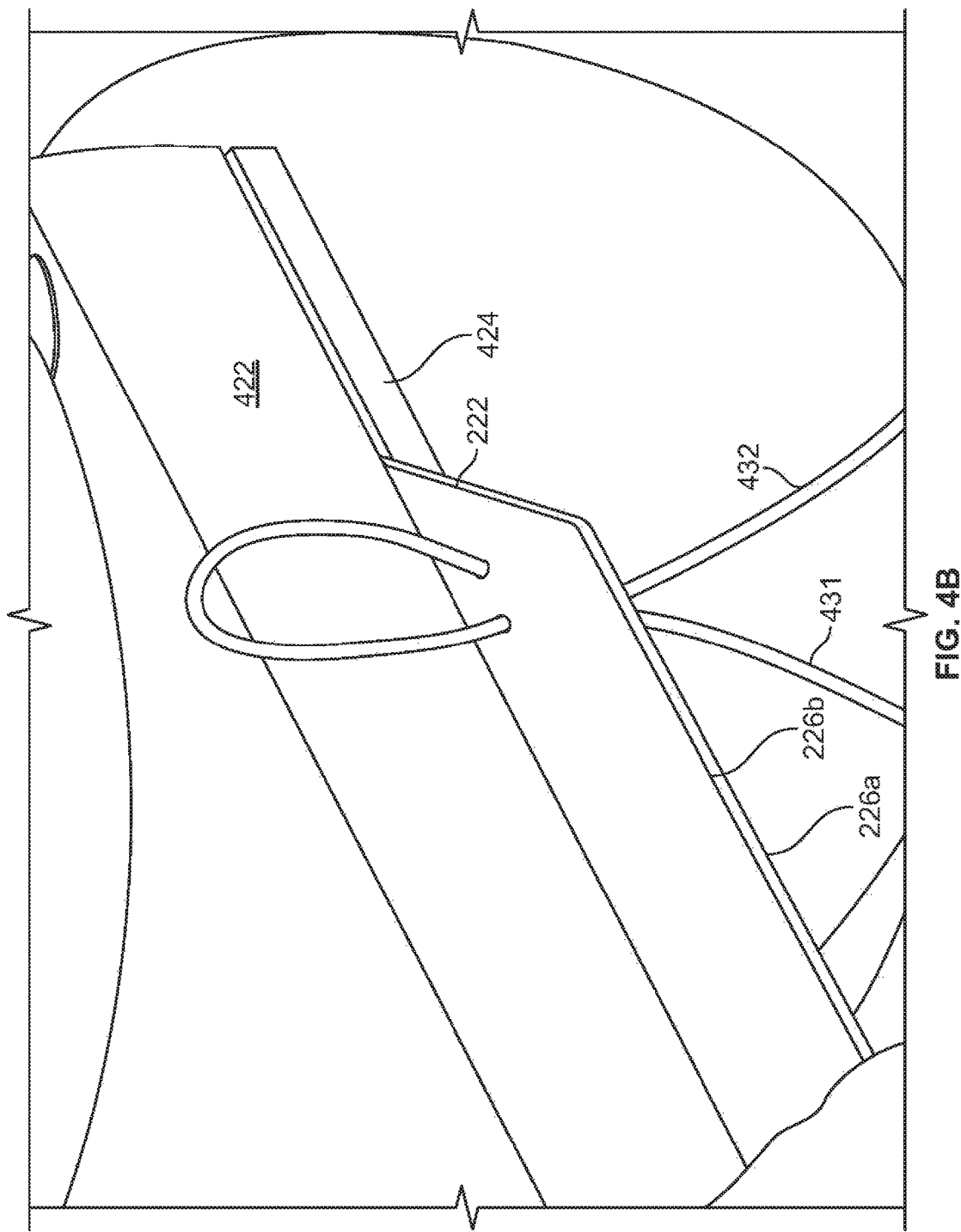
Figure 4D:
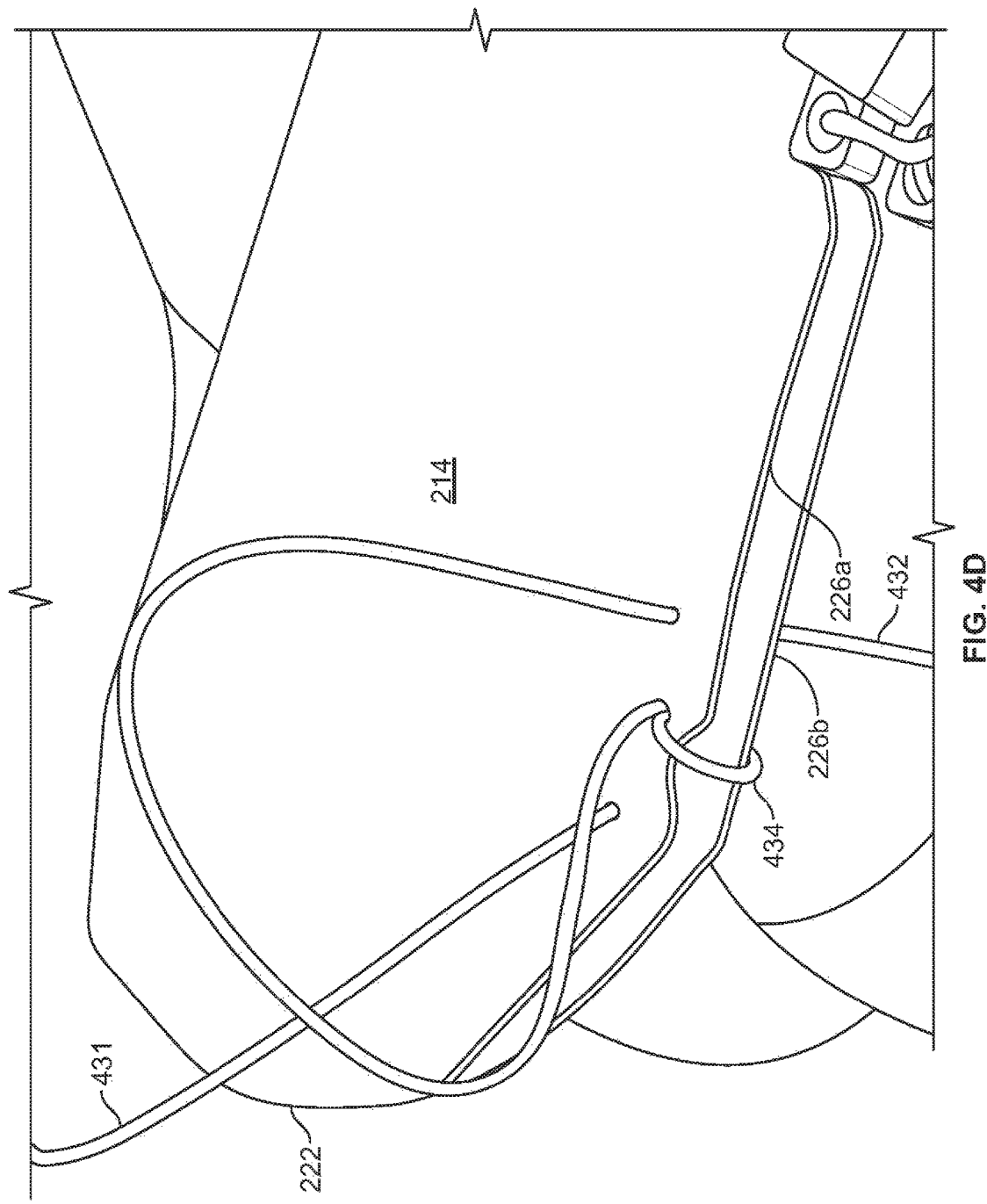
Figure 4F:
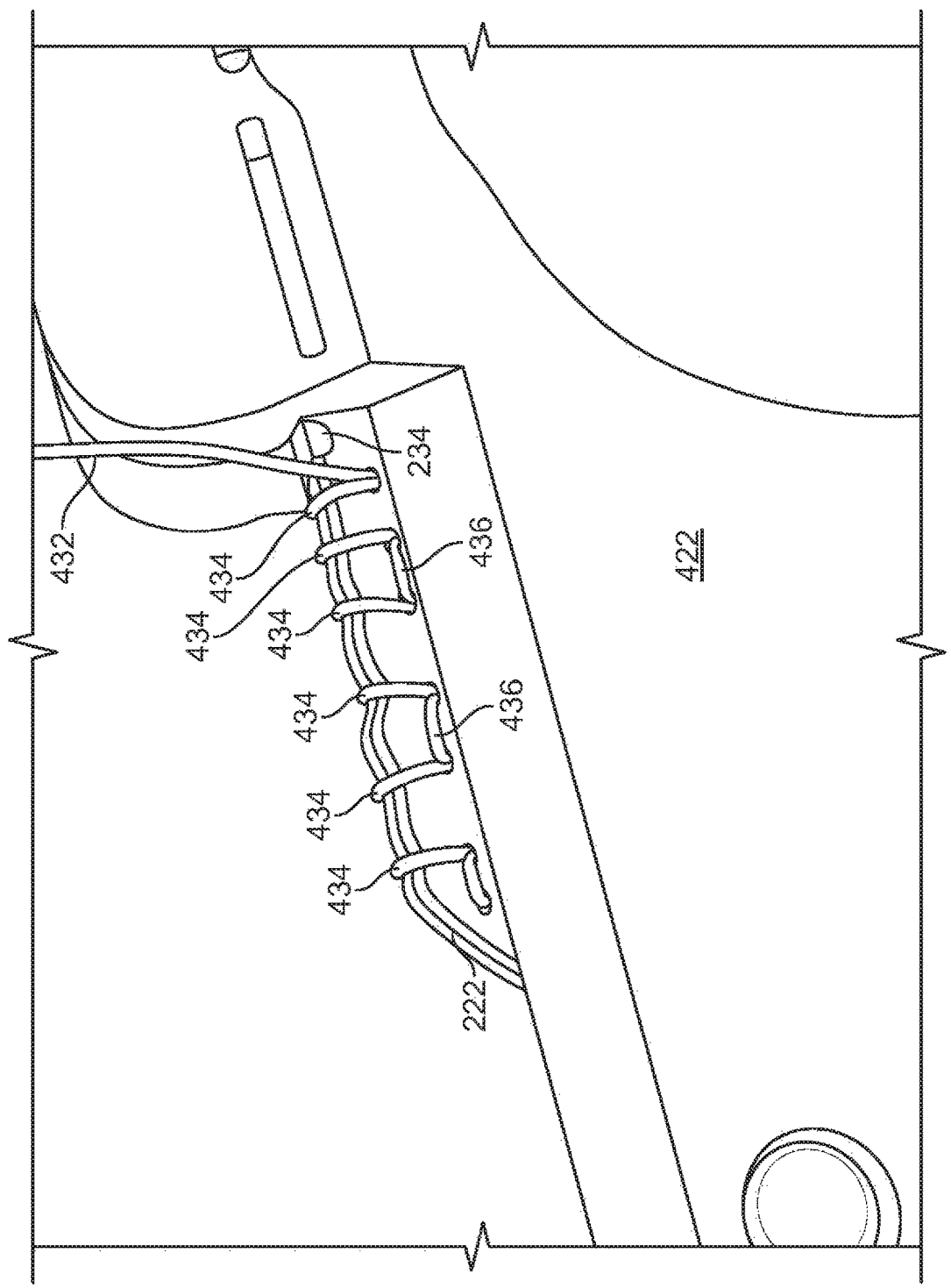

Stitch 446 can be formed in a process depicted in FIGS. 4A-4G. As shown in FIG. 4A, a thread needle 410 can be passed through aligned leaflet side edges 226a and 226b to create a first aperture at a location near bottom edges 222, e.g., a location approximately 1 mm from the bottom edges 222. The leaflet side edges 226a and 226b can be retained in a desired configuration by clamping the leaflets between clamp sides 422 and 424. Needle 410 pulls a leading end 431 of a thread 432 through the first aperture. As shown in FIG. 4B, needle 410 can then form a second aperture adjacent to the first aperture along the stitch line (towards the leaflet sleeve portion) about 0.5 mm away from the first aperture to pull leading end 431 of thread 432 through the second aperture to form a first parallel segment. As shown in FIG. 4C, a perpendicular loop segment 434 can be made by guiding needle 410 around the leaflet side edges and re-enter the second aperture from a backside. Thread 432 can be pulled through the second aperture until it sits firmly against the leaflet material (e.g., leaflet pericardium tissue). FIG. 4D shows a second parallel segment, which can be made by pushing needle 410 through leaflet tissue along the stitch line to form a third aperture approximately 1 mm from the second aperture (towards the sleeve segments of the leaflet). As shown in FIG. 4E, a second perpendicular loop segment 434 can be formed by again having needle 410 loop around the leaflet side edges and reenter the third aperture through the backside. This is repeated up to notch 234 to form a total of six parallel segments 436 and six perpendicular loop segments 434 in a forward direction, as shown in FIG. 4F. The stitch pattern can then be repeated in a reverse direction towards the bottom edges 222 of the leaflets through the previously formed apertures. Accordingly, each aperture can include two perpendicular loop segments 434 and parallel segments on the opposite sides can be formed from the parallel segments that were created in the forward direction, as shown in FIG. 4G. The method and stitches depicted in FIGS. 4A-4G can be applicable to leaflets 200, 300 discussed herein.

Stitch 446 and other stitches provided herein can improve the reliability of a seal formed along a stitch line, create fewer apertures through the leaflets, and simplify the stitching operation. Having fewer apertures can help minimize the occurrence of blood leakage through the apertures. The single continuous line of stitch 446 using a single row of apertures can minimize a width of a side edge portion needed to form a continuous seal along the side edges of the leaflets, thus providing a reduced restricted profile for prosthetic heart valves provided herein. For example, U.S. Pat. No. 8,778,020 describes a variety of ways that leaflets can be sutured together using combinations of whip stitches and running stitches, but these stitches require additional apertures and multiple lines. Perpendicular loop segments 434 can stitch a plurality of leaflets together, similar to the whip stitches discussed in U.S. Pat. No. 8,778,020. Parallel segments 436 can secure valve leaflets to one another, similar to the running stitches discussed in U.S. Pat. No. 8,778,020. Although stitch 446 can provide an improved attachment between side edges of leaflets in prosthetic heart valves provided herein, some embodiments of prosthetic heart valves provided herein can use other stitch patterns, such as those described in U.S. Pat. No. 8,778,020, which is hereby incorporated by reference.

Important characteristics of the thread can include, but are not limited to, tensile strength, abrasion resistance and creep rupture resistance characteristics that allow the device to be delivered and implanted into a human anatomy. The thread used for suturing together portions of the heart valve, e.g., sides edges of the leaflets, can be composed of biocompatible materials that include, but are not limited to, polyethylenes such as ultra high molecular weight polyethylene (UHMWPE), polyesters (PET), and combinations thereof.

Referring back to FIGS. 1A and 1B, prosthetic heart valve 100 can include a tubular seal 130. Tubular seal 130 can be secured to bottom edges 222 (FIG. 2A) of the body portion 214 of at least one leaflet 200 by a circumferential running stitch 134 within prosthetic heart valve 100. Tubular seal 130 can be secured to expandable tubular member 110 by fasteners 136 and extended around the outside of expandable tubular member 110 to provide a seal that minimizes blood leakage around the leaflets 200 of an implanted prosthetic heart valve 100. The structure and materials of tubular seal 130 are discussed below in reference to FIGS. 6 and 7A-7E.

Figure 5A:
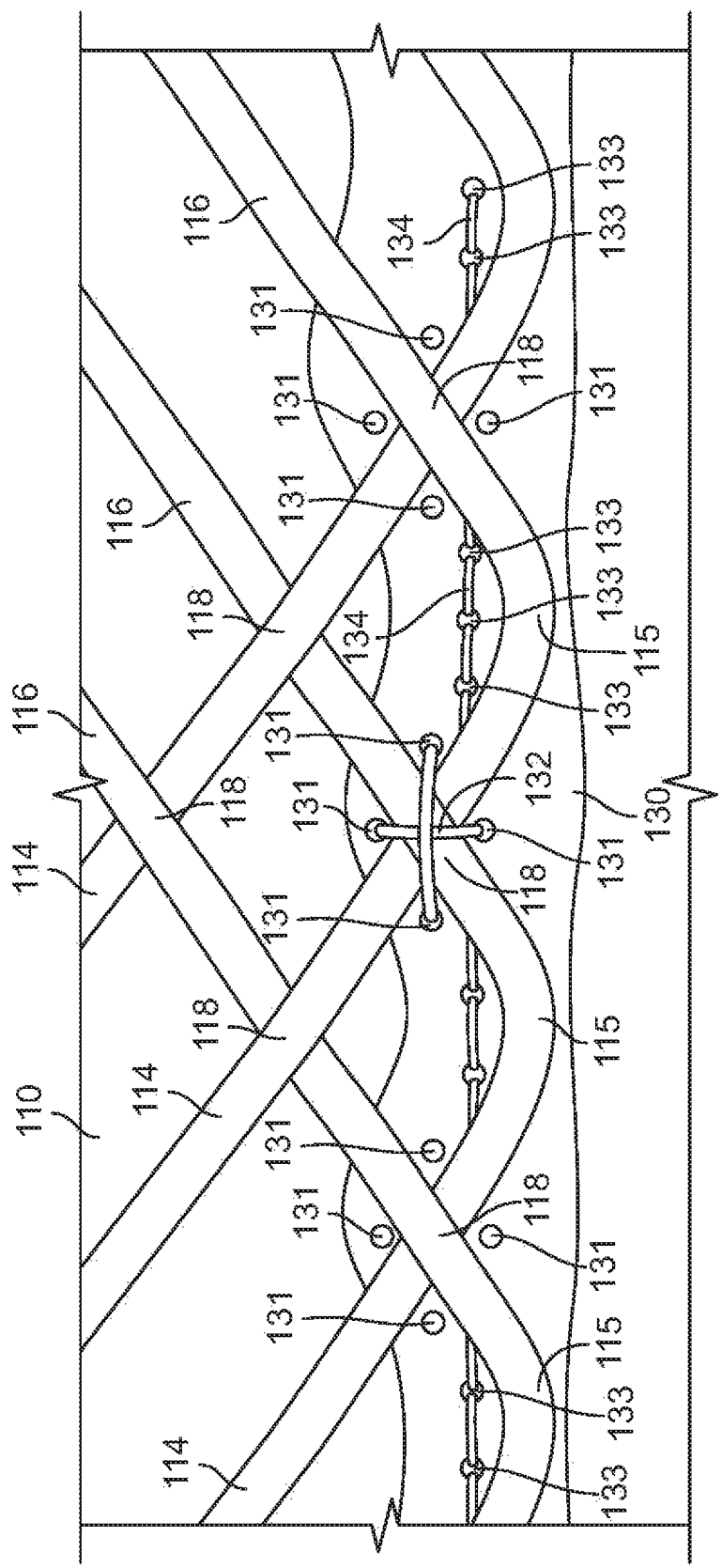
Figure 5B:
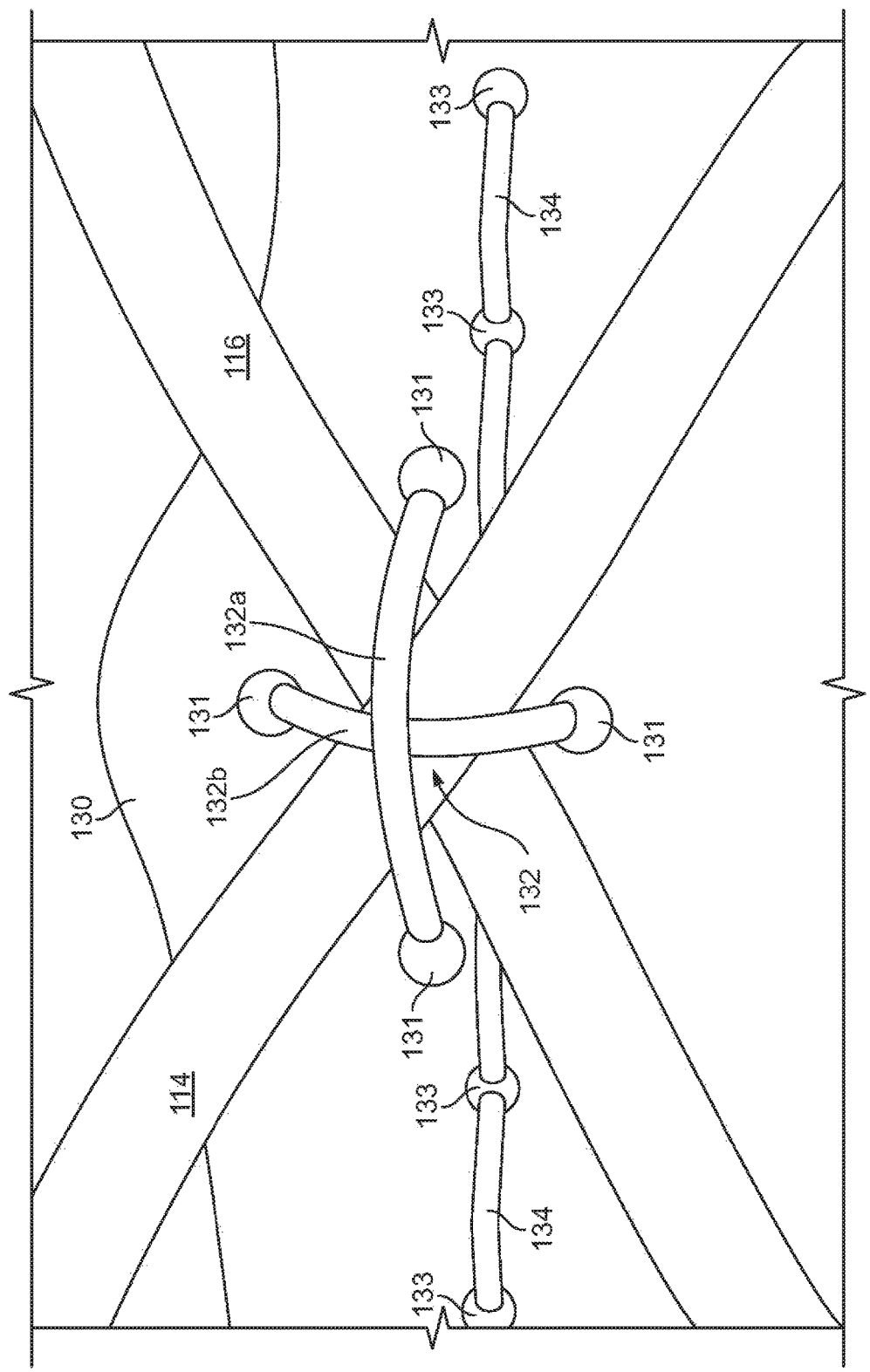

Referring to FIGS. 5A-5C, an improved tubular seal stitching pattern can include a cross stitch 132 between tubular seal 130 and expandable member 110. FIGS. 5A-5C illustrate how the tubular seal 130 can be secured to the expandable member 110, e.g., a braided stent, by a plurality of cross stitches connecting the tubular seal 130 to a pair of overlapping wire members of the braided stent. As shown in FIGS. 1A, 1B and 5A-5C, expandable member 110 can be a braided stent including one or more wires having a first set of segments 114 extending helically in a first direction and a second set of segments 116 extending helically in a second direction such that the first set of segments 114 cross the second set of segments 116 at intersection points 118. As shown, one or more wires can have inflow crowns 115 at an end of the braided stent where the wires transition from first segments 114 to second segments 116. In some cases, cross stitches 132 secure tubular seal 130 at an intersection 118 to two crossing segments 114, 116 of the braided stent. A separate circumferential running stitch 134 can be inserted into preformed apertures 133 to secure the adaptive seal to bottom edges 222 of leaflets 200 shown in FIGS. 2A and 2C. Cross-stitches around the intersections 118 can increase the strength of an attachment of tubular seal 130 to the expandable member 110 while also allowing for improved load transfer to the expandable member 110. In some cases, the cross stitches secure tubular seal 130 at intersections 118 located immediately above (proximal) the inflow crowns 115. Cross stitches 132 can be formed by passing two stitches 132a, 132b of a suture in orthogonal directions over the intersections 118 and through the tubular seal 130. In some cases, preformed apertures 131 for cross stitch 132 can intersection 118 immediately adjacent to inflow crowns 115 is sutured to tubular seal 130 via a cross stitch provided herein. The tubular seal stitching pattern provided herein can increase the strength of the attachment between the tubular seal 130 and the expandable member 110 while also allowing for improved load transfer to the expandable member 110 through the use of the plurality of cross stitches.

Tubular seal 130 can have any suitable structure. In some cases, tubular seal 130 can include an elastic material. In some cases, tubular seal 130 can include one or more layers of an elastomeric polymer. In some cases, tubular seal 130 can include a polycarbonate, polyurethane, silicone, polytetrafluoroethylene (PTFE), or a combination thereof. Other suitable materials include, but are not limited to, natural and synthetic rubbers, including cis-1,4-polyisoprene rubber, styrene/butadiene copolymers, polybutadiene rubber, styrene/isoprene/butadiene rubber, butyl rubber, halobutyl rubber; polyurethane elastomers, including elastomers based on both aromatic and aliphatic isocyanates; flexible polyolefins, including flexible polyethylene and polypropylene homopolymers and copolymers; styrenic thermoplastic elastomers; polyamide elastomers; polyamide-ether elastomers; esterether or ester-ester elastomers; flexible ionomers; thermoplastic vulcanizates; flexible poly(vinyl chloride) homopolymers and copolymers; flexible acrylic polymers; and blends and alloys of these, such as poly(vinyl chloride) alloys like poly(vinyl chloride)-polyurethane alloys. In some cases, tubular seal 130 can include an aliphatic polycarbonate-based thermoplastic urethane. In some cases, tubular seal 130 can include an elastomeric polymer having a hardness ranging from 3.07 MPa to 9.9 MPa, or a durometer ranging from 75 Shore A to 75 Shore D using ASTM standard D2240 in force on Jan. 1, 2014. In some cases, tubular seal 130 can include a polymeric material having the mechanical properties shown in Table I below. Notably, all of the listed ASTM standards refers to the standard in force on Jan. 1, 2014.

TABLE I

|  |  | ASTM Standard |
|---|---|---|
| Durometer Range Available | 75 Shore A-75 Shore D | D2240 |
| Specific Gravity | 1.10-1.14 | D792 |
| Melt Flow | 2-26 g/10 min(205° C./3.26 kg) | D1238 |

|  | MECHANICAL PROPERTY RANGES | | | | ASTM Standard |
|---|---|---|---|---|---|
| Durometer | 75A-B20 | 55D | 75D | 75D | |
| Ultimate Tensile Strength (psi) | 400-9000 | 5000-10000 | 3000-8000 | | D638 |
| Tensile (psi) | | | | | |
| @50% elongation | 350-650 | 1500-1800 | 3000-8000 | | D638 |
| @100% elongation | 550-850 | 1800-2200 | 3000-8000 | | D638 |
| @200% elongation | 600-1200 | 2800-4200 | | | D638 |
| @300% elongation | 1200-2000 | 4200-10000 | | | D630 |
| Ultimate Elongation (%) | 350-750 | 200-400 | 100-300 | | D638 | be formed in the tubular seal 130. In some cases, a portion of the tubular seal 130 that is sutured by cross stitch 132 includes an internal fabric, such as those discussed below. Each cross stitch 132 can be knotted independently. As shown in FIG. 5C, cross stitches 132 each include a separate knot 137. Additionally, cross stitches 132 can be arranged to not pass through leaflets 200. Cross stitches 132 can be repeated at a plurality of intersections 118 (FIG. 5A) circumferentially around an inflow end of a prosthetic heart valve provided herein such that an entire circumference of tubular seal 130 is securely attached. In some cases, each In some cases, referring back to FIG. 1A, tubular seal 130 can include attachment structures to improve the attachment of the tubular seal 130 to leaflets 200 and/or expandable member 110.

Figure 7A:
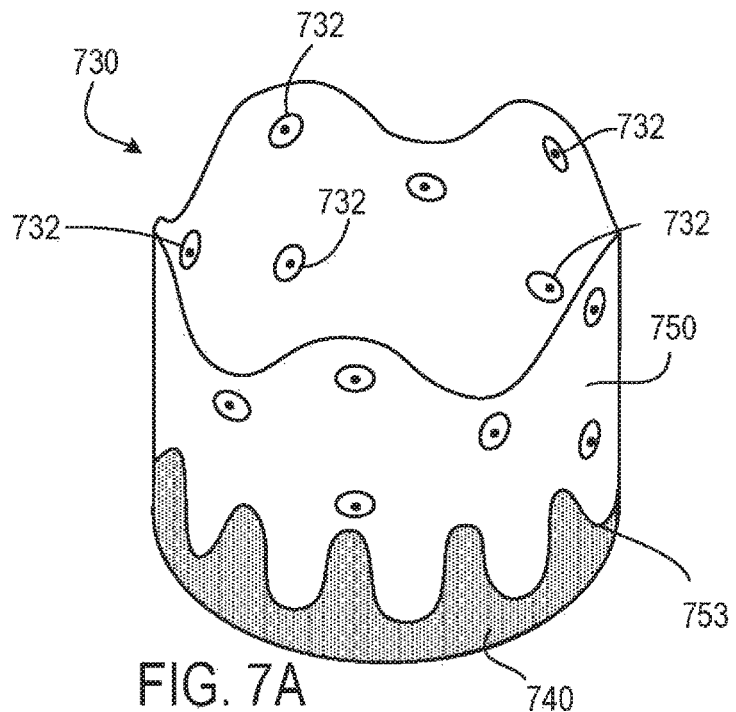
FIGS. 7A-7E depict exemplary tubular seals having a fabric positioned within a matrix that can be used in a prosthetic heart valve provided herein.
Figure 7B:
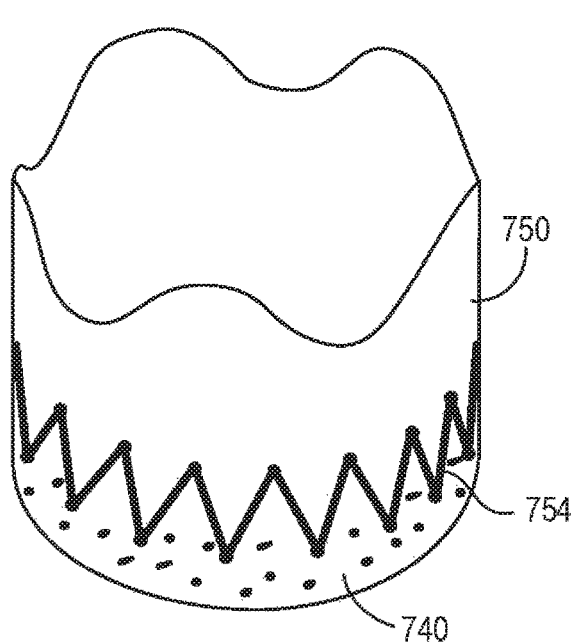

In some cases, as shown in FIG. 7A, a tubular seal 730 can include an inflow end section 740 and an outflow end section 750. The inflow end section 740 can include a fabric embedded within elastomeric material and the outflow end section 750 can include a plurality of grommets 732. The fabric of inflow end section 740 can be a woven material. In some cases, the fabric can have warp threads and/or weft threads. The fabric is composed of fibers having an average thread diameter from about 0.00002 inches to about 0.002 inches (or from about 0.5 microns to about 50 microns), more preferably from about 0.0008 inches to about 0.002 inches (or from about 20 micron to about 40 microns). In some cases, more preferably, the fabric is composed of fibers having a thread diameter of about 0.0011 inches (about 27 microns).

In some cases, the fabric can include non-elastomeric fibers. Suitable non-elastomeric fiber materials include, but are not limited to, polyolefins, polyesters such as PES 38/31 manufactured by SaatiTech, and polyamides. More particularly, the polyolefins may be, for example, one or more of polyethylene, polypropylene, polybutene, ethylene copolymers, propylene copolymers, and butene copolymers. Because the fabric can include non-elastic fibers, inflow end section 740 and outflow end section 750 can have different overall elastic properties. In some cases, tubular seal 730 can be used as a tubular seal 130 of prosthetic heart valve 100, as previously shown in FIG. 1A. In some cases, tubular seal 730 can be used in other prosthetic heart valves provided herein.

Figure 7C:
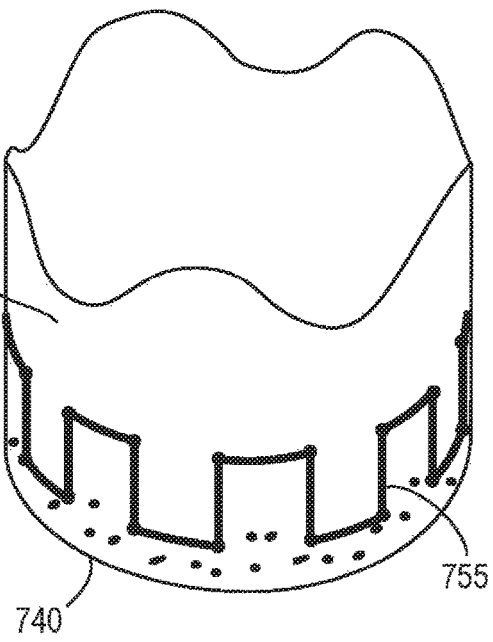
Figure 7D:
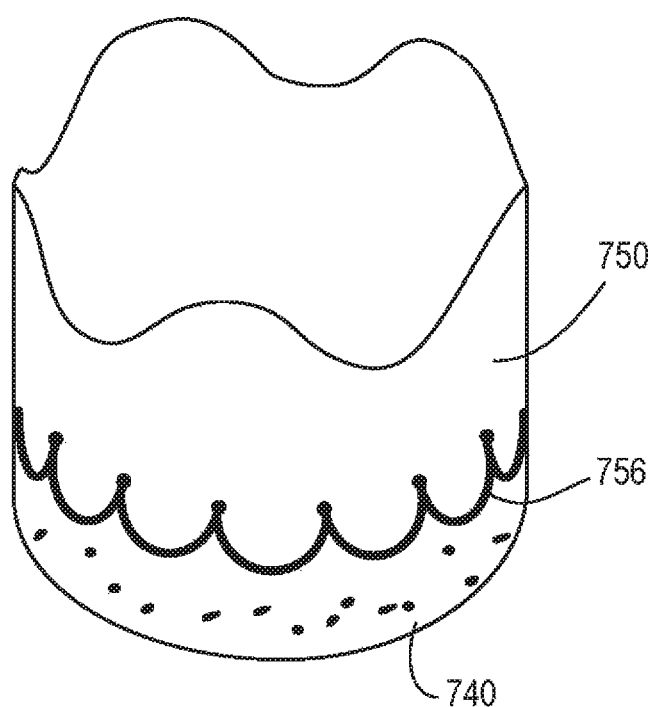

As shown in FIGS. 7A-7D, an interface 753 between the inflow end section 740 and the outflow end section 750 is non-linear due to a non-linear edge of fabric within the inflow end section 740. As shown in FIG. 7A, the non-linear edge can be sinusoidal 753. In some cases, as shown in FIGS. 7C-7D, the non-linear edge can be a zigzagged edge 754, a stepped edge 755, or a scalloped edge 756.

In some cases, inflow end section 740 can be thicker than outflow end section because of the presence of a fabric within inflow end section 740, 750. In some cases, inflow end section 740 can have a thickness of about 0.0028 inches (about 70 microns) and the outflow end section 750 can have a thickness of about 0.0020 inches (about 50 microns). Other suitable thicknesses for the inflow end section include thicknesses ranging from about 0.0020 inches to about 0.0035 inches (about 50 microns to about 90 microns), or more preferably, from about 0.0025 inches to about 0.0031 inches (about 60 microns to about 80 microns). Suitable thicknesses for the outflow end section include thicknesses ranging from about 0.0011 inches to about 0.0028 inches (about 30 microns to about 70 microns), or more preferably, from about 0.0016 inches to about 0.0023 inches (about 40 microns to about 60 microns). In some cases, suitable thickness ratios of the inflow end section relative to the outflow end section can range from 1:1 to 1.2:1, from 1.2:1 to 1.4:1, from 1.4:1 to 1.5:1, and from 1.5:1 to 2:1. A non-linear edge can providing a non-linear interface between the inflow end section 740 and the outflow end section 750. A prosthetic heart valve with the non-linear interface may have an increased overall diameter that tapers more gradually when compared to a prosthetic heart valve that has a linear interface. The non-linear edge of the fabric can also gradually transition the change in elastic properties between the outflow end section 750 and the inflow end section 740, mitigating the formation of stress concentrators along the interface 753 that can cause tearing in the tubular member. Additionally, the shape of non-linear interface 753 can limit the propagation of tears.

In some cases, the fabric can be arranged in the inflow end section 740 to allow for the fabric within inflow end section 740 to stretch in axial and/or radial directions to allow the tubular seal to stretch along with an expandable member during implantation. When the fabric does not allow the tubular seal to adequately stretch, the seal can cause non-uniform crimping during manufacturing or damage the expandable member during device deployment. In some cases, a woven fabric can be arranged to have the warp and the waft extend in directions oblique to the axis of the tubular seal. This can allow the fabric to flex in radial and/or axial directions relative to the axis of the tubular seal, but limit the fabric from stretching in a direction oblique to the axis. In some cases, both the warp and the waft can extend at an angle between 30 degrees and 60 degrees with the axis of the tubular seal. In some cases, both the warp and the waft can extend at an angle between 5 degrees and 70 degrees with the axis of the tubular seal. In some cases, the warp and waft can be arranged within the tubular member 730 to form an angle of about 45 degrees with the axis of the tubular seal. In some cases, the fabric can be a knit fabric arranged to allow for a predetermined amount of stretch in the axial and/or radial directions. Limiting the fabric within inflow end section 740 from stretching in a direction oblique to the axis can prevent the fabric from bunching and minimize non-uniform crimping during manufacturing.

Additional exemplary tubular seals including a fabric and grommets are described in U.S. Patent Application No. 2013/0090729, which is hereby incorporated by reference in its entirety. For example, U.S. Pat. No. 8,778,020 describes a seal that includes a multilayer, cylindrical seal body having projections alternating with recesses along the proximal edge of the seal body with proximal reinforcing grommets and a distal reinforcing band, which may be formed from a woven or nonwoven fabric and either incorporated within the interior of the multilayer seal body or adhered to the surface thereof.

In some cases, tubular seals described in U.S. Patent Application No. 2013/0090729 can be modified to include a fabric arrangement that allows a seal to stretch in axial and/or radial directions. In some cases, elastomeric materials provided herein can be incorporated into the tubular seals disclosed in U.S. Patent Application No. 2013/0090729. In some cases, the tubular seals described in U.S. Patent Application No. 2013/0090729 can be modified to include the non-linear interface 753 provided herein.

Referring back to FIG. 7A, tubular seal 730 can be created by producing one or more layers of elastomeric polymer, applying the fabric and grommets 732 to the one or more layers of elastomeric polymer, and overcoating the fabric and grommets 732 with one or more additional layers of elastomeric material. In some cases, different layers can have different elastomeric properties. In some cases, tubular seals (e.g., 130, 730, or 760) can include a radially innermost layer including at least one elastomeric polymer, e.g., a polycarbonate and a polyurethane; a radially outermost layer including at least one elastomeric polymer, e.g., a polycarbonate and a polyurethane; and at least one inner layer disposed between the radially outermost layer and a radially innermost layer. In some cases, the modulus of elasticity of the innermost layer is less than the modulus of elasticity of the radially innermost outer layer and the modulus of elasticity of the radially outermost outer layer. In some cases, the elongation to break of the inner layer is greater than the elongation to break of the radially innermost outer layer and the elongation to break of the radially outermost outer layer. Although the radially innermost outer layer and the radially outermost outer layer have been depicted as including the same material, it will be appreciated that they may be compositionally the same or different.

The multilayer tubular seals provided herein (e.g., 130, 730, 760) may be formed in a variety of ways. In some cases, multilayer tubular seals provided herein may be formed by successive applications of a polymer solution to an appropriately shaped mandrel, such as that illustrated in FIG. 6. Following a careful cleaning of the mandrel 600, the mandrel may be mounted to an appropriate holding fixture in a spray booth. A first coating composition including a carrier and at least one polymer may be applied to the mandrel 600 and subsequently dried to form a first coated mandrel. In some cases, the first coating composition includes one or more elastomeric polymers, e.g, polycarbonate and/or a polyurethane, and a volatile carrier. The coating composition may be applied as a single layer or multiple layers to achieve the desired dried coating thickness. The grommets 732 (FIG. 7A) and the fabric may be positioned on the first coated mandrel by inserting locating pins 620 in apertures 610 in the tapered mandrel 600 which align with corresponding perforations 30 provided in the grommets 32, 34, 36 and the fabric 40. In FIG. 6, only one pin 620 has been illustrated for clarity. In some instances, it may be desirable to secure the plurality of grommets 732 and the fabric to the mandrel or to an underlying coating layer by applying a drop of a first coating composition, or other adhesive composition, to each item to ensure that it remains properly positioned during subsequent processing. The fabric can be cut to a suitable shape having a non-linear edge using any suitable method. In some cases, the fabric can be die cut. In some cases, the fabric can be cut with a blade. In some cases, the fabric can be cut using a femtosecond laser. In some cases, a femtosecond laser cut fabric mitigate the chances of forming stress concentrators along the edge of the fabric.

A second coating composition including a carrier and at least one polymer may be applied to the first coated mandrel, the fabric, and the plurality of grommets. In some cases, the second coating composition includes one or more elastomeric polymers, e.g, polycarbonate and/or a polyurethane, and a volatile carrier. The carrier of the second coating composition may be removed, thereby forming a second coated mandrel. The second coating composition may be applied as a single layer or as multiple layers to achieve the desired dried coating thickness. In some cases, the second coating composition may be different from the first coating composition. In some cases, the second coating composition may be composed of the same material as the first coating composition.

In some cases, a third coating composition including a carrier and at least one polymer may be applied to the second coated mandrel. In some cases, the third coating composition includes one or more elastomeric polymers, e.g, polycarbonate and/or a polyurethane, and a volatile carrier. The carrier of the third coating composition may be removed thereby forming a tubular seal precursor. The third coating composition may be applied as a single layer or as multiple layers to achieve the desired dried coating thickness. In some cases, the third coating composition may be different from the first coating composition. In some cases, the third coating composition may be the same as the first coating composition. In some cases, the third coating composition may be different from the second coating composition. In some cases, the third coating composition may be the same as the second coating composition. Following removal of the carrier from the third coating composition, the tubular seal precursor may be inspected to ensure that it is fully formed and meets dimensional specifications, such as a thickness specification. In some cases, a suitable thickness for the tubular seal precursor can range from about 0.001 inches to about 0.0030 inches (about 30 microns to about 75 microns) or from about 0.002 inches to about 0.0047 inches (about 50 microns to about 120 microns). Other suitable thicknesses for the tubular seal precursor include a range from about 0.0008 inches to about 0.002 inches (about 20 microns to about 40 microns), about 0.001 inches to about 0.002 inches (about 30 microns to about 50 microns), about 0.002 inches to about 0.0029 inches (about 50 microns to about 75 microns), about 0.002 inches to about 0.004 inches (about 50 microns to about 100 microns), about 0.004 inches to about 0.0047 inches (about 100 microns to about 120 microns), about 0.004 inches to about 0.0059 inches (about 100 microns to about 150 microns), about 0.0059 inches to about 0.0079 inches (about 150 microns to about 200 microns), as well as any thickness value within any of the listed ranges.

In some cases, the tubular seal precursor may be inspected to ensure that it meets certain functional specifications, e.g., tensile and frictional specifications. The tubular seal precursor may then be trimmed by laser cutting, or blade cutting, to conform to dimensional specifications and removed from the tapered seal-forming mandrel as a formed tubular seal. In some cases, at least some preformed apertures for suturing tubular seal to expandable member 110 and/or leaflets 200 can be performed by laser cutting. In some cases, at least some of the grommets may be formed by a laser cutting operation performed on a tubular seal precursor. In some cases, grommets 732 of FIG. 7A may be added to the multilayer, generally cylindrical seal, in a step not illustrated, as a proximal band. Subsequent laser cutting of the tubular seal precursor would then simultaneously form grommets 732 by removing the portions of the proximal band located between the projections.

In some cases, coating compositions may be selected to provide a relatively stiff dried polymer such as a dried polymer having a Shore D hardness of about 55, or a hardness of about 6.21 Megapascals (Mpa). In some cases, coating compositions may be selected to provide a relatively elastomeric dried polymer such as a dried polymer having a Shore A hardness of about 80, or a hardness of about 3.45 MPa. In some cases, the first and third dried polymer layers may have a Shore D hardness of 55, or a hardness of 6.21 MPa, and the second layer may have a Shore A hardness of 80, or a hardness of 3.45 MPa.

Although in some cases described above, three polymer layers were employed, it will be appreciated that a greater or lesser number of layers may be employed and that each of the three or more layers may include two or more sublayers. In some cases, the plurality of grommets and the fabric can be positioned between the first and second coating layers. In some cases, the plurality of grommets and the fabric can be positioned elsewhere within the tubular seal, e.g., within a layer, or on the radially innermost or radially outermost surface of the tubular seal.

The mandrel 600 of FIG. 6 includes a taper which results in a tubular seal having a slightly smaller diameter proximal end compared to the diameter of the distal end. In some cases, the diameter of the proximal end can include a diameter reduction of about 3% to about 30% as compared to the diameter of the distal end. The taper allows the tubular seal to be removed from the mandrel with relative ease upon completion of the fabrication process. The smaller proximal diameter of the tubular seal tends to cause the proximal projections to lie more firmly against an anchor element of the replacement heart valve. In some cases, the surface of the mandrel may be textured to create a tubular seal with a reduced contact area. In some cases, the mandrel can be textured using a bead blasting process. In combination with the selection of a relatively hard outer layer, a textured seal surface is believed to result in a lower friction surface.

Figure 7E:
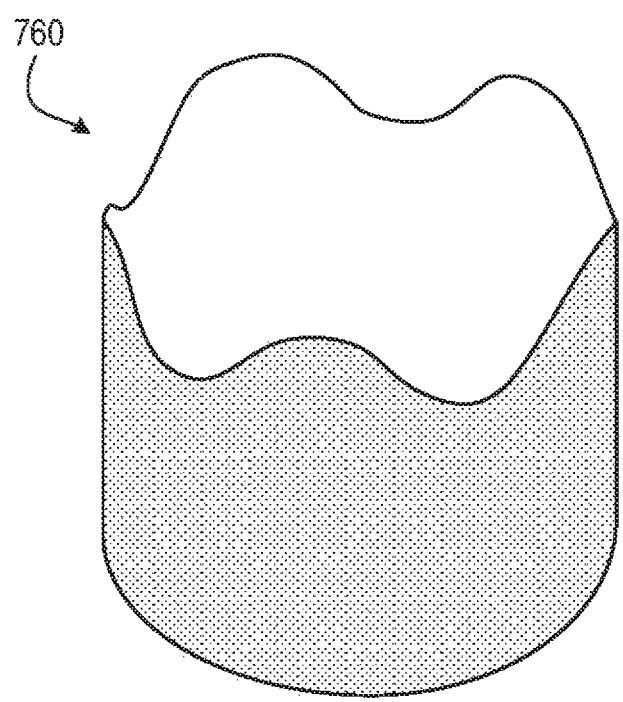

As shown in FIG. 7E, a tubular seal 760 can include a woven or non-woven fabric embedded throughout a polymer or metal matrix structure. In some cases, at least one leaflet of the heart valve can be secured to the tubular seal in a portion of the tubular seal including the woven or non-woven fabric to minimize blood leakage between the tubular seal and the leaflets.

In some cases, the matrix structure can be made of elastomeric material. In some cases, tubular seal 760 can be made of the fabric alone. The fabric can include non-elastic fibers arranged to allow for the tubular seal 760 to stretch in axial and/or radial directions relative to the axis of the tubular seal 760. In some cases, the non-elastic fibers can be arranged within the tubular member 760 to form an angle of about 45 degrees with the axis of the tubular seal. In some cases, the fabric can be a knit fabric arranged to allow for a predetermined amount of stretch in the axial and/or radial directions. In some cases, the fabric can be made of polymeric materials that include, but are not limited to, polyesters, polyolefins such as polyethylene and polypropylene, polyamides, nylons, and combinations thereof. In some cases, the fabric can have a thickness ranging from about 0.002 inches to about 0.003 inches (about 40 to about 80 microns). In some cases, the fabric can be woven such that spacings between individual fibers create openings in the fabric that together constitutes from about 20% to about 40% of a fabric surface.

A number of embodiments of the invention have been described. Nevertheless, it will be understood that various modifications may be made without departing from the spirit and scope of the invention. Accordingly, other embodiments are within the scope of the following claims.

What is claimed is:

1. A prosthetic heart valve comprising:
   an expandable member comprising one or more braided wires, the one or more braided wires comprising a first set of wire segments extended helically in a first direction and a second set of wire segments extended helically in a second direction such that each wire segment of the first set intersects a plurality of wire segments from the second set at a plurality of intersection points, wherein the one or more braided wires have crowns where the wire segments of the first set connect to wire segments of the second set;
   a plurality of leaflets being secured within the expandable member; and
   a tubular seal comprising an elastomeric material, the tubular seal having an inflow edge being secured to bottom inflow edges of the plurality of leaflets and to the expandable member by a plurality of sutures, characterized by the sutures comprising cross stitches formed around both a wire segment of the first set and a wire segment of the second set at one of the intersection points.

2. The prosthetic heart valve of claim 1, wherein each cross stitch is an independently tied off stitch unconnected to other cross stitches.

3. The prosthetic heart valve of claim 1, wherein each cross stitch is attached at an intersection point immediately adjacent a crown at an inflow side of the expandable member.

4. The prosthetic heart valve of claim 1, wherein the plurality of leaflets are secured together along side edges thereof.

5. The prosthetic heart valve of claim 4, wherein the plurality of leaflets each comprise two sleeve portions, wherein the sleeve portions are secured to the expandable member by a plurality of anchor elements.

6. The prosthetic heart valve of claim 1, wherein the tubular seal comprises a plurality of non-elastic fibers retained within a matrix of the elastomeric material, the non-elastic fibers being arranged to allow the tubular seal to stretch in an axial or a radial direction.

7. The prosthetic heart valve of claim 6, wherein the non-elastic fibers are part of a fabric.

8. The prosthetic heart valve of claim 7, wherein the fabric has a thickness ranging from about 40 to about 80 microns.

9. The prosthetic heart valve of claim 7, wherein the fabric is a woven fabric.

10. The prosthetic heart valve of claim 9, wherein the woven fabric comprises fibers in a warp direction and fibers in a waft direction, wherein the fibers in both the warp direction and the waft direction are angled with respect to a central axis of the tubular seal.

11. The prosthetic heart valve of claim 10, wherein the fibers in both the warp direction and the waft direct are angled at an angle between 5 degrees and 70 degrees with respect to the central axis of the tubular seal.

12. The prosthetic heart valve of claim 7, wherein the fibers are made of polyester.

13. The prosthetic heart valve of claim 6, wherein the non-elastic fibers are uniformly dispersed throughout the matrix.

14. The prosthetic heart valve of claim 1, wherein the tubular seal has a substantially uniform thickness.

15. A prosthetic heart valve comprising:
   an expandable member comprising one or more braided wires, the one or more braided wires comprising a first set of wire segments and a second set of wire segments such that each wire segment of the first set intersects a plurality of wire segments from the second set at a plurality of intersection points;
   a plurality of leaflets being secured within the expandable member; and
   a tubular seal comprising an elastomeric material, the tubular seal having an inflow edge being secured to bottom inflow edges of the plurality of leaflets and to the expandable member by a plurality of sutures, wherein the sutures comprise cross stitches formed around both a wire segment of the first set and a wire segment of the second set at one of the intersection points;
   wherein the tubular seal comprises an outflow end region and an inflow end region, the inflow end region being a portion of the tubular seal comprising a fabric within a matrix of an elastomeric matrix, wherein the fabric has a non-linear edge defining an interface between the inflow end region and the outflow end region.

16. The prosthetic heart valve of claim 15, wherein the non-linear edge of the fabric has a sinusoidal or scalloped shape.

17. The prosthetic heart valve of claim 15, wherein the plurality of leaflets are secured to the tubular seal by a continuous circumferential running stitch.

18. The prosthetic heart valve of claim 15, wherein the first set of wire segments extends helically in a first direction and a second set of wire segments extends helically in a second direction.

19. The prosthetic heart valve of claim 18, wherein the one or more braided wires have crowns where the wire segments of the first set connect to wire segments of the second set.

* * * * *